(12) United States Patent
Ducatt et al.

(10) Patent No.: US 9,675,523 B2
(45) Date of Patent: Jun. 13, 2017

(54) PRESCRIPTION CONTROL SYSTEM

(71) Applicants: James Dean Ducatt, Lake Clear, NY (US); Justin Aiello, Kennebunk, ME (US)

(72) Inventors: James Dean Ducatt, Lake Clear, NY (US); Justin Aiello, Kennebunk, ME (US)

( * ) Notice: Subject to any disclaimer, the term of this patent is extended or adjusted under 35 U.S.C. 154(b) by 0 days.

(21) Appl. No.: 14/836,267

(22) Filed: Aug. 26, 2015

(65) Prior Publication Data

US 2015/0359711 A1    Dec. 17, 2015

Related U.S. Application Data

(63) Continuation-in-part of application No. 14/469,266, filed on Aug. 26, 2014, now Pat. No. 9,542,534.

(60) Provisional application No. 61/869,956, filed on Aug. 26, 2013.

(51) Int. Cl.
| | |
|---|---|
| *G06F 17/00* | (2006.01) |
| *A61J 7/00* | (2006.01) |
| *G07F 17/00* | (2006.01) |
| *G07F 11/00* | (2006.01) |
| *G07F 11/58* | (2006.01) |
| *G07F 11/62* | (2006.01) |
| *G06F 19/00* | (2011.01) |

(52) U.S. Cl.
CPC ............ *A61J 7/0076* (2013.01); *G06F 19/30* (2013.01); *G07F 11/002* (2013.01); *G07F 11/005* (2013.01); *G07F 11/58* (2013.01); *G07F 11/62* (2013.01); *G07F 17/0092* (2013.01); *A61J 2200/30* (2013.01)

(58) Field of Classification Search
None
See application file for complete search history.

(56) References Cited

U.S. PATENT DOCUMENTS

| | | | |
|---|---|---|---|
| 2,493,616 | A | 1/1950 | Burns |
| 4,054,343 | A | 10/1977 | Heyland |
| 4,953,745 | A | 9/1990 | Rowlett, Jr. |

(Continued)

FOREIGN PATENT DOCUMENTS

| | | |
|---|---|---|
| WO | 2005/105015 A1 | 11/2005 |
| WO | 2013/033033 A1 | 3/2013 |

*Primary Examiner* — Prasad Gokhale
(74) *Attorney, Agent, or Firm* — Woods Oviatt Gilman LLP; Dennis B. Danella, Esq.

(57) ABSTRACT

A medication dispensing device comprises a cartridge unit and a control unit. The cartridge unit comprises a cartridge housing defining a dispensing channel to allow passage of the dosage from the cartridge to the patient. A cartridge holds dosages, with a driven member engaging the cartridge. The driven member drives the cartridge to dispense a dosage. The control unit comprises a main housing for coupling to the cartridge housing. A driver member engages the driven member to actuate the driven member. A motor driven locking mechanism is moveable between locked and unlocked positions. When in the locked position the cartridge unit is secured to the control unit. When in the unlocked position the cartridge unit is separable from the control unit thereby providing access to the cartridge. A mobile computing device stores dosage availability and receives an authorized patient identification input before dispensing a dosage.

19 Claims, 16 Drawing Sheets

(56) References Cited

U.S. PATENT DOCUMENTS

| | | |
|---|---|---|
| 5,097,652 A | 3/1992 | Inamura et al. |
| 5,522,525 A | 6/1996 | McLaughlin et al. |
| 5,597,995 A | 1/1997 | Williams et al. |
| 5,737,539 A | 4/1998 | Edelson et al. |
| 5,752,723 A | 5/1998 | Robertson |
| 5,810,198 A | 9/1998 | Townsend et al. |
| 5,845,264 A | 12/1998 | Nellhaus |
| 6,004,020 A | 12/1999 | Bartur |
| 6,021,392 A | 2/2000 | Lester et al. |
| 6,066,374 A | 5/2000 | Healy et al. |
| 6,145,697 A | 11/2000 | Gudish |
| 6,161,711 A | 12/2000 | Miceli et al. |
| 6,421,650 B1 | 7/2002 | Goetz et al. |
| 6,438,451 B1 | 8/2002 | Lion |
| 6,558,956 B1 | 5/2003 | Carron et al. |
| 6,578,003 B1 | 6/2003 | Camarda et al. |
| 6,587,829 B1 | 7/2003 | Camarda et al. |
| 6,769,228 B1 | 8/2004 | Mahar |
| 6,842,736 B1 | 1/2005 | Brzozowski |
| 6,851,615 B2 | 2/2005 | Jones |
| 6,859,780 B1 | 2/2005 | Cunningham |
| 6,868,344 B1 | 3/2005 | Nelson |
| 6,871,783 B2 | 3/2005 | Kaafarani et al. |
| 6,952,681 B2 | 10/2005 | McQuade et al. |
| 7,017,748 B2 | 3/2006 | Weinstein |
| 7,100,793 B2 | 9/2006 | Baum |
| 7,108,153 B2 * | 9/2006 | Wood .................... A61J 7/0076 221/105 |
| 7,124,031 B1 | 10/2006 | Hoffman et al. |
| 7,184,897 B2 | 2/2007 | Nelson |
| 7,260,402 B1 | 8/2007 | Ahmed |
| 7,263,411 B2 | 8/2007 | Shows et al. |
| 7,295,890 B2 | 11/2007 | Jean-Pierre |
| 7,328,919 B2 | 2/2008 | Weinstein |
| 7,359,765 B2 | 4/2008 | Varvarelis et al. |
| 7,395,214 B2 | 7/2008 | Shillingburg |
| 7,426,476 B2 | 9/2008 | Munoz et al. |
| 7,427,002 B2 | 9/2008 | Liff et al. |
| 7,513,367 B2 | 4/2009 | Wolpow |
| 7,574,370 B2 | 8/2009 | Mayaud |
| 7,584,018 B2 | 9/2009 | Shows et al. |
| 7,668,730 B2 | 2/2010 | Reardan et al. |
| 7,672,884 B2 | 3/2010 | Schuster et al. |
| 7,729,927 B2 | 6/2010 | Cunningham |
| 7,735,681 B2 | 6/2010 | Handfeld et al. |
| 7,765,106 B2 | 7/2010 | Reardan et al. |
| 7,765,107 B2 | 7/2010 | Reardan et al. |
| 7,783,379 B2 | 8/2010 | Beane et al. |
| 7,797,171 B2 | 9/2010 | Reardan et al. |
| 7,844,361 B2 | 11/2010 | Jean-Pierre |
| 7,844,362 B2 | 11/2010 | Handfield et al. |
| 7,860,603 B2 | 12/2010 | Handfield et al. |
| 7,895,059 B2 | 2/2011 | Reardan et al. |
| 7,917,246 B2 | 3/2011 | Handfield et al. |
| 7,930,064 B2 | 4/2011 | Popovich |
| 7,970,622 B2 | 6/2011 | Lilly et al. |
| 7,996,105 B2 | 8/2011 | Handfield et al. |
| 8,032,397 B2 | 10/2011 | Lawless |
| 8,060,246 B2 | 11/2011 | Berg |
| 8,061,351 B2 | 11/2011 | Dave |
| 8,086,470 B2 | 12/2011 | Siegel |
| 8,091,320 B2 | 1/2012 | Mahar |
| 8,099,301 B2 | 1/2012 | Keresman, III et al. |
| 8,112,175 B2 | 2/2012 | Handfield et al. |
| 8,117,071 B1 | 2/2012 | Fitch et al. |
| 8,190,291 B2 | 5/2012 | Beane et al. |
| 8,202,217 B2 | 6/2012 | Howell et al. |
| 8,219,418 B2 | 7/2012 | Lilly et al. |
| 8,269,635 B2 | 9/2012 | Kroll et al. |
| 8,269,636 B2 | 9/2012 | Kroll et al. |
| 8,333,053 B2 | 12/2012 | Mahar |
| 8,335,697 B2 | 12/2012 | Siegel |
| 8,342,400 B1 | 1/2013 | Reese |
| 8,348,144 B2 | 1/2013 | Thorsson et al. |
| 8,359,271 B2 | 1/2013 | Peckover |
| 8,386,277 B2 | 2/2013 | Hearnes, II et al. |
| 8,417,378 B2 | 4/2013 | Joslyn |
| 8,417,381 B2 | 4/2013 | Vonk et al. |
| 8,457,988 B1 | 6/2013 | Reardan et al. |
| 8,464,947 B2 | 6/2013 | Swan et al. |
| 8,479,988 B2 | 7/2013 | Louie et al. |
| 8,489,417 B2 | 7/2013 | Hoffman et al. |
| 8,498,879 B2 | 7/2013 | Michon et al. |
| 8,514,067 B2 | 8/2013 | Hyde et al. |
| 8,556,120 B2 | 10/2013 | Ando et al. |
| 8,600,548 B2 | 12/2013 | Bossi et al. |
| 8,636,172 B2 | 1/2014 | Dunn |
| 8,670,865 B2 | 3/2014 | Coe |
| 2003/0183642 A1 | 10/2003 | Kempker, Sr. |
| 2006/0124656 A1 | 6/2006 | Popovich |
| 2006/0266763 A1 | 11/2006 | Bech |
| 2007/0186923 A1 * | 8/2007 | Poutiatine ............ A61J 7/0038 128/200.14 |
| 2009/0192648 A1 | 7/2009 | Namineni et al. |
| 2009/0281657 A1 | 11/2009 | Gak et al. |
| 2010/0145506 A1 | 6/2010 | Waugh et al. |
| 2011/0202174 A1 | 8/2011 | Bogash et al. |
| 2011/0270442 A1 * | 11/2011 | Conley ................ G06F 19/3462 700/237 |
| 2011/0315705 A1 * | 12/2011 | Ando .................... A61J 7/0076 221/9 |
| 2012/0085775 A1 | 4/2012 | Czarnek |
| 2012/0165975 A1 | 6/2012 | Yi et al. |
| 2013/0253700 A1 | 9/2013 | Carson et al. |
| 2014/0162598 A1 * | 6/2014 | Villa-Real ............... H04M 1/66 455/411 |
| 2014/0214200 A1 | 7/2014 | Chrusciel et al. |
| 2014/0249669 A1 | 9/2014 | Puliga et al. |
| 2014/0278510 A1 * | 9/2014 | McLean ................ A61J 7/0076 705/2 |
| 2015/0073590 A1 * | 3/2015 | Garcia Manchado . G06Q 20/18 700/232 |
| 2015/0291344 A1 * | 10/2015 | Macvittie ............... A61J 7/0472 221/13 |

\* cited by examiner

PRESCRIPTION CONTROL SYSTEM

CROSS-REFERENCE TO RELATED APPLICATIONS

This application is a continuation-in-part of pending U.S. patent application Ser. No. 14/469,266, filed Aug. 26, 2014, and entitled "Prescription Control System", which claims the benefit of U.S. Provisional Patent Application No. 61/869,956 filed Aug. 26, 2013, the contents of which are fully incorporated by reference herein.

BACKGROUND OF THE INVENTION

The present invention relates to a prescription control system for regulating the dispensing of medications; more particularly, the present invention is directed to a prescription control system for regulating the dispensing of addictive pharmaceutical agents such as narcotics, wherein the system includes a pill dispenser with a simplified delivery device and a number of safety systems, including audio and visual recording and tamper warning capabilities.

The highly addictive properties of many medications can pose a large threat to patients prescribed these medications by medical personnel, such as doctors or nurse practitioners. While these medications are considered controlled substances, the only layer of control is between the manufacturer and the pharmacy. Control is lost once the pharmacy distributes the narcotics to the patient.

In an attempt to create additional control, prescription narcotics have warnings that doctors and pharmacists are required by law to explain to the patient. Unfortunately, there is no way to ensure that the patient will follow these warnings. This inability to regulate the patient's use of prescription narcotics makes it easy for noncomplying patients to enter a cycle of drug abuse, such as that outlined in FIG. 1.

Everyone is subject to the danger of becoming addicted. Addiction is not selective or isolated to any social or economic class and does not age discriminate. Anybody may become an addict, even if they have no initial intentions of becoming addicted. Patients from all walks of life are handed a 28 to 30 day supply of medication, given the warnings, and instructed to use the medication only as prescribed. The problem is that the addictive properties of these medications can make it difficult for the patient to heed the warnings and abide by the prescription.

If addiction takes its hold on a patient, the results can be devastating. Often, the first step is that the patient will progressively run out of their medication within shorter and shorter periods of time; a 30 day prescription may be consumed in 20 days while the next 30 day supply may be consumed in an even shorter amount of time, such as 10 to 15 days. As patients seek to replenish their supply, they may begin to "shop" for medications by making up stories about how their medication was lost, damaged, or stolen. They may ask doctors for early refills or in some cases seek to buy the drug from illegal street vendors at exorbitant prices.

Patients can become so addicted that they will beg, borrow, and steal to get more of the medication. When all else fails, they may feel forced by the nature of their addiction to turn to non-pharmaceutical drugs such as heroin or cocaine. This often leads to legal problems where the patients may end up in drug court, with the ultimate result being that the government becomes responsible for providing and paying for rehabilitation. In worst cases, a patient may die due to an overdose.

Accordingly, there exists a need for a device which dispenses controlled substances, such as narcotics, only at the rate designated by the prescribing doctor. This device should be portable so as to provide proper regulation of the patient's drug regimen without requiring the patient to be tied to a non-portable, home-based medication dispenser. The present invention fills these and other needs.

SUMMARY OF THE INVENTION

The present invention is directed to a medication dispensing device for dispensing a dosage of a medication to a patient. The dosage is dispensed to the patient upon receipt of a valid request, the valid request including an authorized patient identification input and a dosage availability determined in accordance with a medical professional's prescription. In one aspect, the medication dispensing device comprises a case defining a medication holding area and a dosage holding area, the dose holding area including an entry end and a dispensing end. A first gate is located at the entry end between the medication holding area and the dosage holding area, and is operable to selectively open to allow the dosage to pass from the medication holding area to the dosage holding area. A second gate is located at the dispensing end and is operable to selectively open to allow the dosage to pass from the dosage holding area to a retrieval area accessible to the patient. A central processing unit (CPU) is disposed within the case and includes a memory, wherein the dosage availability is stored in memory. A patient authentication device is in communication with the CPU, and is configured to receive the authorized patient identification input. A battery is configured for providing electrical energy to the CPU. Upon receipt of the valid request, the CPU operates to: i) open the first gate to pass the dosage to the dosage holding area; ii) close the first gate after the dosage has passed to the dosage holding area; iii) open the second gate after the first gate has closed to dispense the dosage to the patient; and iv) close the second gate after the dosage has been dispensed to the patient.

In another aspect, the first gate and the second gate are each operably coupled to first and second actuators, respectively, wherein each of first and second actuators are powered by the battery to selectively open its respective gate upon receiving the respective command from the CPU. The medication dispensing device may further comprises a photogate associated with the dosage holding area, wherein the photogate is operable to initiate a control signal to the CPU when the dosage interrupts the photogate so that the CPU closes the first gate. Also, a camera and microphone may be provided for recording video data and audio data in the memory upon receipt of an unauthorized patient identification input.

In another aspect, the medication dispensing device may further comprise a tray for holding the medication, wherein the tray is configured to be positioned within the medication holding area. The tray may include a dispensing slot configured to coincide with the first gate, and the dispensing slot may be proportioned so that only a single dosage may pass through the dispensing slot at a time. The case may include a tray shutter operable to selectively open to allow loading of the tray within the medication holding area, and a tray shutter locking pin to secure the tray shutter in a closed position. The tray shutter locking pin is retractable to allow the tray shutter to open for loading of the tray. The case may further define a dosage retrieval area, wherein the dosage passes into the dosage retrieval area after passing through the second gate. Further, the case may include a retrieval shutter operable to selectively open to allow the patient to remove the dosage from the dosage retrieval area. A retrieval shutter locking pin may secure the retrieval shutter in a closed position, wherein the retrieval shutter locking pin is retractable to allow the retrieval shutter to open. The medication dispensing device may further comprises a vibrating motor associated with the medication holding area, wherein the vibrating motor is powered by the battery upon receipt of the valid request to aid transport of the dosage to and through the first gate.

In another aspect, the case may include a first panel and a second panel having first and second sidewalls, respectively. Each of the first and second sidewalls may include at least one pair of corresponding case contacts that form a completed circuit when the first and second panels are disposed together. The CPU operates to secure at least one of the first and second gates in the closed position upon severing of the completed circuit.

In yet another aspect, the device may further include a camera and microphone, wherein the camera and microphone operate to record video data and audio data in the memory upon severing of the completed circuit. Further, the device may include a wireless transceiver that operates to transmit the video and audio data to a remote monitoring server. In addition, a global positioning system (GPS) node may be provided to transmit a location of the device to the remote monitoring server upon severing of the completed circuit. The device may also include a camera, microphone and touchscreen display, wherein the CPU is operable to initiate a videoconferencing application program to remotely engage with a medical professional via a videoconference session.

In another aspect, a medication dispensing device is provided that includes a case including a medication delivery system for selectively holding the medication and delivering the dosage to the patient. A CPU is disposed within the case and including a memory, wherein the dose availability is stored in the memory. A patient authentication device is in communication with the CPU and configured to receive the authorized patient identification input. A camera is configured to record video data in the memory, and a microphone configured to record audio data in the memory. A battery is configured for providing electrical energy to the CPU. Upon receipt of the valid request, the CPU operates the medication delivery system to deliver the dosage to the patient. Upon receipt of an invalid request, the camera and microphone operate to record video data and audio data in the memory, wherein the invalid request includes an unauthorized patient identification input at the patient authentication device. Further, the case may include a first panel and a second panel, wherein the first panel includes a first sidewall, and the second panel includes a second sidewall. Each of the first and second sidewalls include at least one pair of corresponding case contacts that form a completed circuit when the first and second panels are disposed together, wherein the camera and the microphone operate to record video data and audio data in the memory upon severing of the completed circuit.

In yet another aspect, a medication dispensing device is provided that includes a case including a medication delivery system configured for selectively holding the medication and delivering the dosage to the patient. The case further includes a first panel and a second panel, wherein the first panel includes a first sidewall, and the second panel includes a second sidewall. Each of the first and second sidewalls includes at least one pair of corresponding case contacts that form a completed circuit when the first and second panels are disposed together. A CPU is disposed within the case and includes a memory, wherein the dose availability is stored in the memory. A camera is configured to record video data in the memory, and a microphone is configured to record audio data in the memory. A battery is configured for providing electrical energy to the CPU. Upon receipt of the valid request, the CPU operates the medication delivery system to deliver the dosage to the patient, and the camera and microphone operate to record video data and audio data in the memory upon severing of the completed circuit.

In a further aspect of the present invention, a medication dispensing device comprises a cartridge unit and a control unit. The cartridge housing has a bottom surface and an upwardly extending sidewall defining a cartridge receiving area with the sidewall further defining a dispensing channel formed therethrough to allow passage of the dosage from the cartridge receiving area to the patient. A cartridge is configured to reside within the cartridge receiving area and hold one or more dosages. A driven member is positioned within the cartridge receiving area and is configured to engage the cartridge with the driven member being selectively actuatable to drive the cartridge so as to cause dispensing of a next sequential dosage through the dispensing channel. The control unit comprises a main housing configured for removable coupling to the cartridge housing and having a top surface and a downwardly extending sidewall defining a controller receiving area. The downwardly extending sidewall is configured to coincide with the upwardly extending sidewall of the cartridge housing to prevent access to the cartridge receiving area and the controller receiving area. A driver member is positioned with the controller receiver area and is configured to engage the driven member such that actuation of the driver member upon receipt of the valid request operates to actuate the driven member. A motor driven locking mechanism is moveable between locked and unlocked positions, wherein when in the locked position the cartridge unit is secured to the control unit and wherein when in the unlocked position the cartridge unit is separable from the control unit thereby providing access to the cartridge. A mobile computing device includes a central processing unit (CPU) and a memory, wherein the dosage availability is stored in the memory and the mobile computing device is configured to receive the authorized patient identification input. A battery is configured for providing electrical energy to the driver member and the motor driven locking mechanism.

In still a further aspect, a medication dispensing device comprises a cartridge unit and a control unit. The cartridge unit comprises a cartridge housing having a bottom surface and an upwardly extending sidewall defining a cartridge receiving area. The sidewall further defines a dispensing channel formed therethrough to allow passage of the dosage from the cartridge receiving area to the patient. A cartridge is configured to reside within the cartridge receiving area and hold one or more dosages. The cartridge includes a plurality of walls in spaced parallel relation with one another and extending generally perpendicular to the dispensing channel. A back wall extends across a rear edge of the plurality of wells to thereby define a plurality of dosage wells wherein each well is configured to contain a stack of dosages. A respective dispensing wheel is positioned at a forward edge of the plurality of wells wherein each dispensing wheel includes a recess configured to receive a single dosage at a time from its respective stack. A driven member is positioned within the cartridge receiving area and is configured to engage the cartridge and wherein the driven member is coupled to the dispensing wheels. Upon receipt of a valid request the driver member is energized to drive rotation of the driven member and dispensing wheels so as to advance each respective recess until the next sequential dosage becomes aligned with the dispensing channel thereby dispensing the dosage. The control unit comprises a main housing configured for removable coupling to the cartridge housing and having a top surface and a downwardly extending sidewall defining a controller receiving area. The downwardly extending sidewall is configured to coincide with the upwardly extending sidewall of the cartridge housing. When coupled to the sidewalls prevent access to the cartridge receiving area and the controller receiving area. A driver member is positioned within the controller receiver area and is configured to engage the driven member such that actuation of the driver member upon receipt of the valid request operates to actuate the driven member. A mobile computing device includes a central processing unit (CPU) and a memory, wherein the dosage availability is stored in the memory. The mobile computing device is configured to receive the authorized patient identification input and a battery is configured to provide electrical energy to the driver member and the motor driven locking mechanism.

In yet another aspect, a prescription control system is provided. The system includes a medication filling device configured to sort and count one or more medications; a tray configured to engage the medication filling device, wherein a selected medication is sorted, counted and loaded onto the tray; and a medication dispensing device for dispensing a dosage of the selected medication to a patient. The dosage is dispensed to the patient upon receipt of a valid request. The medication dispensing device comprises a case defining a medication holding area and a dosage holding area, wherein the dose holding area includes an entry end and a dispensing end. The case includes a tray shutter operable to selectively open to allow loading of the tray within the medication holding area. The device further includes a first gate located at the entry end between the medication holding area and the dosage holding area. The first gate is operable to selectively open to allow the dosage to pass from the medication holding area to the dosage holding area. The device includes a second gate located at the dispensing end that is operable to selectively open to allow the dosage to pass from the dosage holding area to a retrieval area accessible to the patient. The device includes a CPU disposed within the case and including a memory, wherein the dosage availability is stored in memory. The device includes a patient authentication device in communication with the CPU that is configured to receive the authorized patient identification input, and a battery configured for providing electrical energy to the CPU. Upon receipt of the valid request, the CPU operates to: i) open the first gate to pass the dosage to the dosage holding area; ii) close the first gate after the dosage has passed to the dosage holding area; iii) open the second gate after the first gate has closed to dispense the dosage to the patient; and iv) close the second gate after the dosage has been dispensed to the patient.

Additional objects, advantages and novel features of the present invention will be set forth in part in the description which follows, and will in part become apparent to those in the practice of the invention, when considered with the attached figures.

BRIEF DESCRIPTION OF THE DRAWINGS

The accompanying drawings form a part of the this specification and are to be read in conjunction therewith, wherein like reference numerals are employed to indicate like parts in the various views, and wherein.

DETAILED DESCRIPTION OF THE INVENTION

Figure 1:
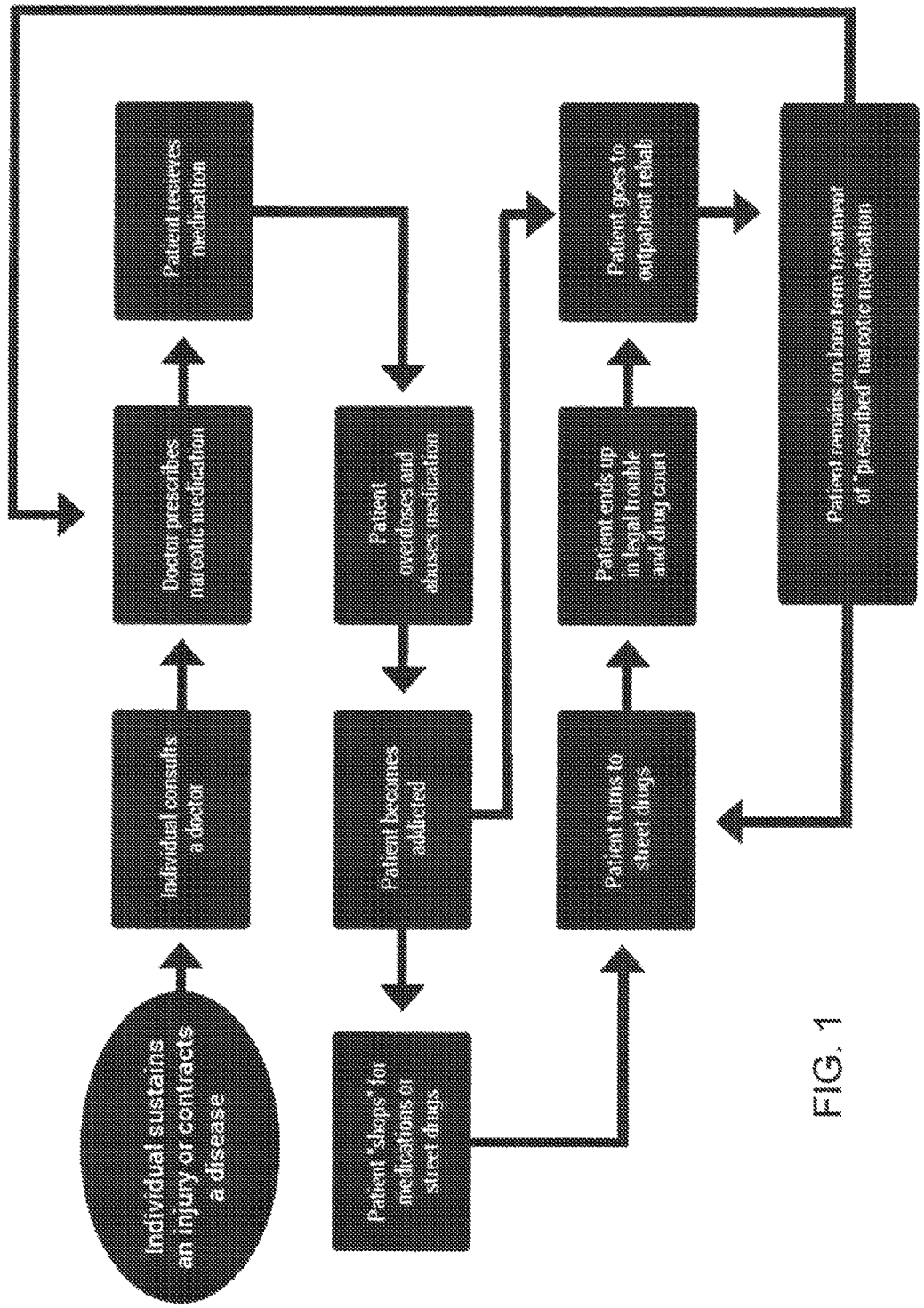
FIG. 1 is a flow diagram illustrating the cycle of abuse suffered by patients that become addicted to one or more medications.
Figure 2:
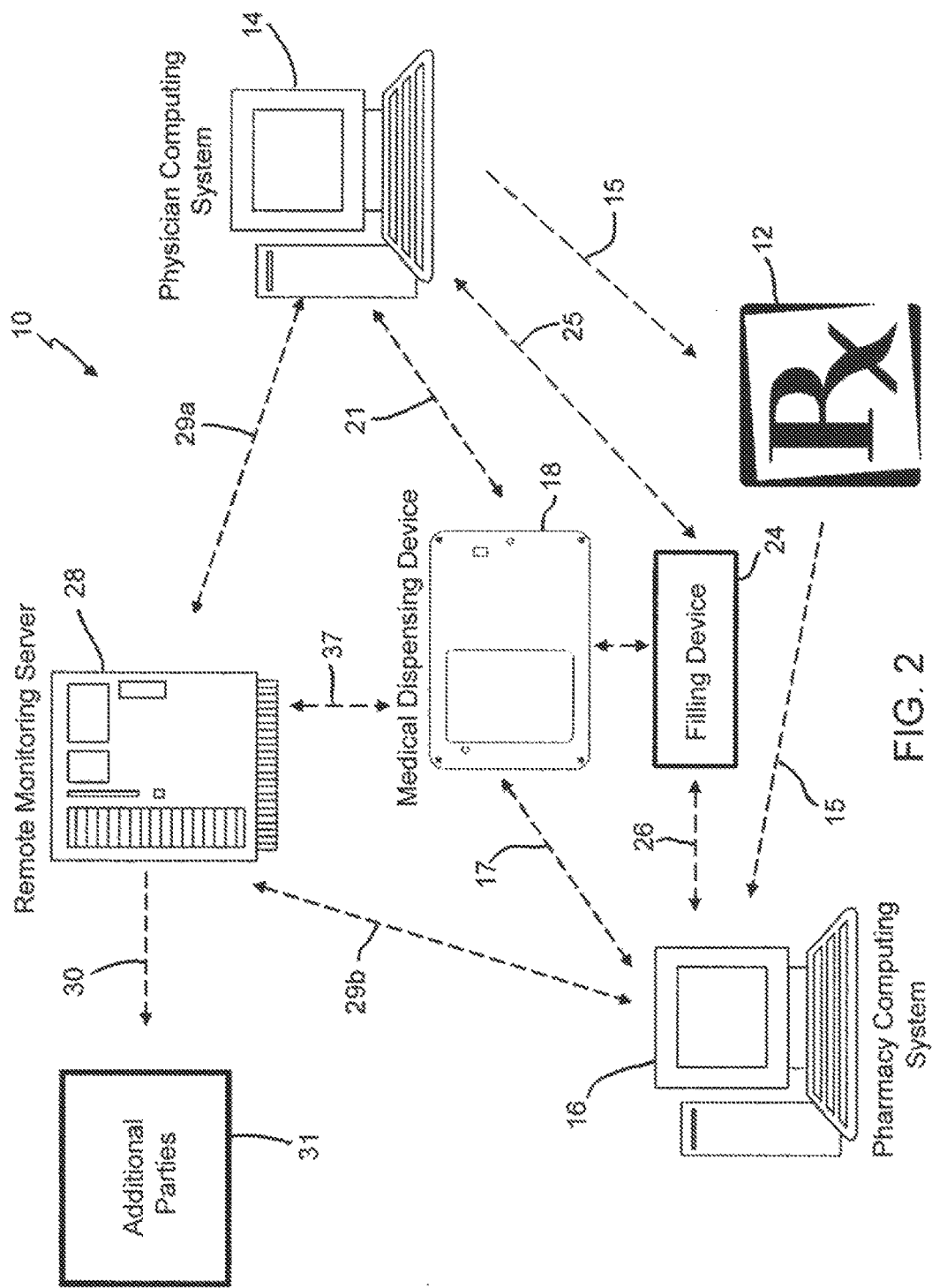
FIG. 2 is a system schematic of an embodiment of a prescription control system in accordance with an aspect of the present invention.

Referring now to the drawings in detail, and specifically to FIG. 2, a schematic of a prescription control system in accordance with an aspect of the present invention is generally designated by reference numeral 10. Following surgery or after being involved in an accident or some other traumatic event, for instance, a patient may receive a prescription 12 from his or her treating physician/trained medical professional ("physician" or "doctor"). This prescription may be for a medication known to lead to addiction, such as a narcotic. Prescription 12 may be a hardcopy prescription slip or may be an electronic prescription. Patient data (such as, but not limited to, name, birth date, purported symptoms, etc.) and prescription data (such as, but not limited to, medication name(s), dosage data, etc.) may be entered onto a physician's computing system 14, which then communicates 15 this data to a designated pharmacy computing system 16 for processing and fulfillment. While the present invention will be described with regard to electronic communications, such as those exchanged through a wireless network or over the Internet, it should be understood by those skilled in the art that all or some of such communications may include exchange of hardcopy materials, such as a traditional written prescription, and such hardcopy communications are to be regarded as within the scope of the present invention.

Figure 3A:
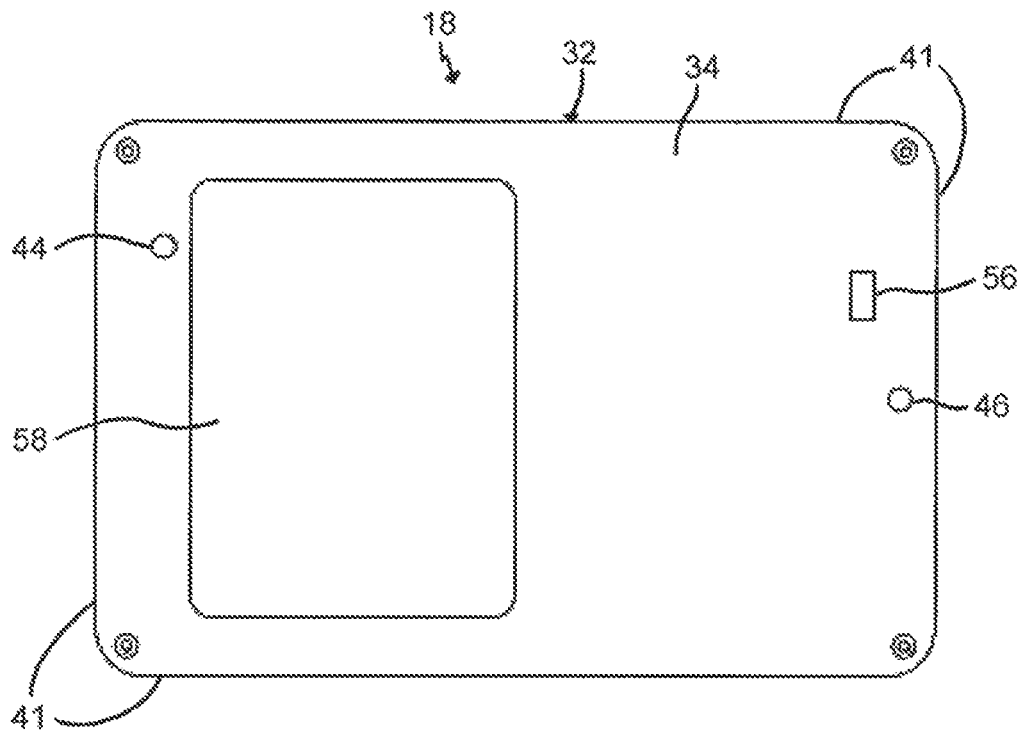
FIG. 3A is a plan view of an embodiment of a medication dispensing device used within the prescription control system shown in FIG. 2.
Figure 3B:
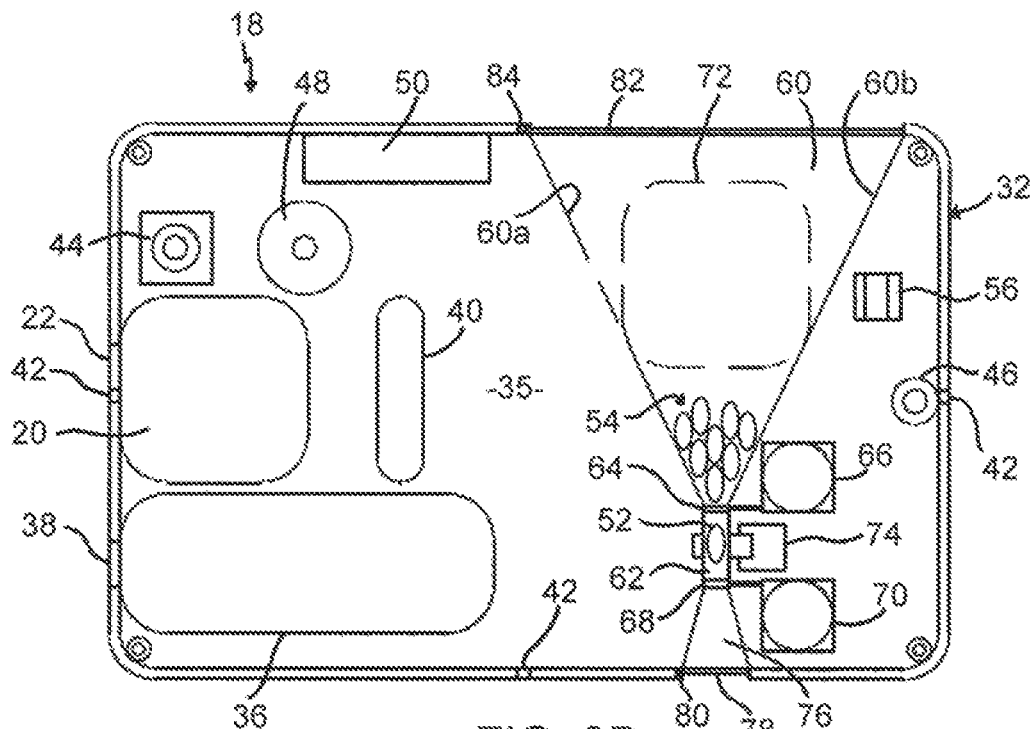
FIG. 3B is an internal plan view of the components comprising the medication dispensing device shown in FIG. 3A.
Figure 3C:
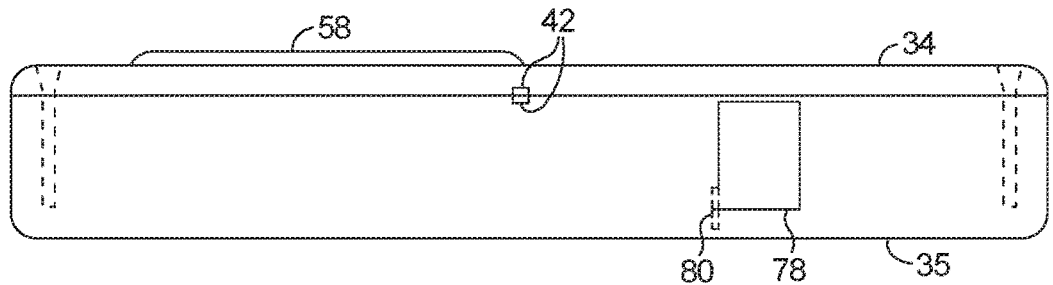
FIG. 3C is a side view of the medication dispensing device used within the prescription control system shown in FIG. 2.
Figure 4:
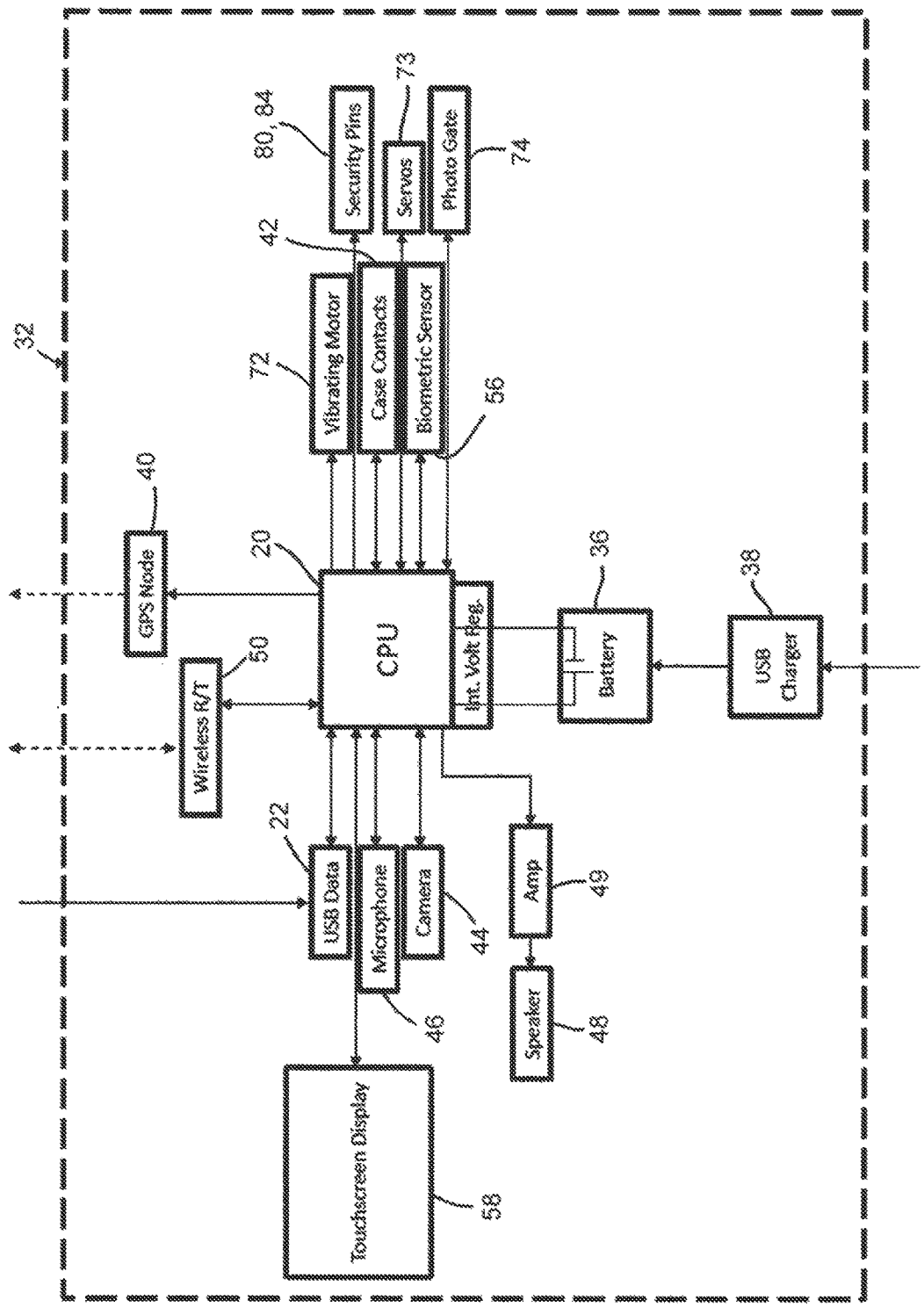
FIG. 4 is a block diagram showing communication pathways of the components comprising the medication dispensing device shown in FIGS. 3A-3C.

After prescription 12 is received by pharmacy computing system 16, pharmacy computing system 16 uploads 17 information related to the prescription, such as the prescription data and patient data, received from physician's computing system 14 or from a traditional written prescription 12 to a hand-held medication dispensing device 18. This information can be uploaded by populating an onboard central processing unit (CPU) 20 having on-chip internal memory storage, as seen in FIGS. 3B and 4. Alternatively, CPU 20 may operate to access a separate external memory storage module housed within medication dispensing device 18. In another aspect, the information related to the prescription may be uploaded 21 to medication dispensing device 18 directly form physician's computing system 14 or may be manually entered into medication dispensing device 18 by the pharmacist who received and is charged with filling prescription 12 ordered by the prescribing physician. As described, uploading of the information or data related to the prescription into the memory of CPU 20 may be conducted through wireless connectivity or may be conducted through a wired connection, such as through a USB data port 22. Medication dispensing device 18 is then loaded with the prescribed type and number of medication as per the prescription's orders.

The prescribed medication may be either manually loaded into medication dispensing device 18 by a pharmacist or it may be loaded 23 via a medication filling device 24 in accordance with a further aspect of the present invention. Medication filing device 24 may also independently receive the electronically transmitted prescription 12 either directly from physician's computing system 14 via communication 25, from pharmacy computing system 16 filling the prescription ordered by the prescribing physician via communication 26, or it may be manually entered into medication filling device 24 device by the pharmacist who received and is charged with filling the prescription. Medication filling device 24 can then assist the pharmacist in filling the prescription, such as by mechanically sorting and counting the prescribed medication. The sorted and counted medication can then be directly loaded into medication dispensing device 18 or may be loaded onto a tray 27 for verification by the pharmacist before tray 27 is loaded into medication dispensing device 18. A more detailed description of a tray 27 in accordance with this aspect of the present invention will be provided below with regard to FIG. 5. Medication filling device 24 may also be used to program medication dispensing device 18 with the patient data and prescription data through a hardware/software interface via a hard wire connection or wirelessly.

As will be discussed in more detail below, medication dispensing device 18 will only dispense a dosage of medication upon receipt of a valid request. A valid request includes input of an authorized patient identification input or access code (discussed below) and requires a dosage availability in accordance with the directions provided by prescription 12 that is stored in the memory of medication dispensing device 18. By way of example, if a dosage may be taken 4 times daily, medication dispensing device 18 will define a dosage availability as a dosage retrieval once every 6 hours (plus or minus a margin of time, such as, for example, 15 to 30 minutes) plus any emergency doses allocated by the prescription, i.e. a limited number of doses in addition to those regularly scheduled as per prescription 12. Emergency doses may be requested at any time until all such emergency doses have been exhausted by the patient, at which point no additional emergency doses will be available and the patient will only be able to receive regularly scheduled doses until a new prescription is obtained and stored with the memory of medication dispensing device 18. A third party vendor, which may include a remote monitoring server 28, may be responsible for servicing and monitoring medication dispensing device 18 and may receive 29a, 29b prescription data from physician's computing system 14 and/or pharmacist's computing system 16 and monitor patient compliance and medication dispensing device 18 integrity (described below) to ensure that the patient is adhering to prescription 12. Should indications warrant (such as a physical breach of the medication dispensing device 18), remote monitoring server 28 may communicate 30 such information to additional parties 31, such as law enforcement entities, for appropriate intervention/action.

Turning now to FIGS. 3A, 3B, 3C and 4, medication dispensing device 18 generally includes a case 32 having a front panel 34 and a back panel 35. Medication dispensing device 18 is powered by a rechargeable battery 36. Battery 36 may be recharged through a USB charge port 38. After a predetermined time period of non-activity, CPU 20 will place the battery and other components within device 18 in a low energy state. If the battery level drops below a first programmed level, an alarm will sound on the device using a speaker 48 and/or an alert will be shown on a display 58. If the battery level drops to a second programmed level device 18 will report 37 the event or alarm (hereinafter "event") to remote monitoring server 28 and power down. CPU 20 will automatically reboot to the last programmed state when the battery level is increased by charging above the first programmed level, and communicate 37 this event to remote monitoring server 28 to inform vendor that device 18 is back online. While offline, reserve power from battery 36 will allow for a global positioning system (GPS) ping from node 40 until battery 36 is completely discharged. Medication dispensing device 18 can only be manually powered down via an override request issued by remote monitoring server 28 when it is intended that medication dispensing device 18 be placed in storage. The override request allows the vendor to access a power down protocol stored in the memory of CPU 20 so as to deactivate medication dispensing device 18.

Front and back panels 34, 35 include corresponding intermediate sides which join to form completed side walls 41 of case 32. In accordance with an aspect of the invention, case 32 is proportioned so as to be a portable, hand-held unit. By way of example, case 32 may be configured to be no more than about 3 inches (7.5 cm) wide, about 5 inches (12.5 cm) long and about 1 inch (2.5 cm) deep. Intermediate sides 41 of both front and back panels 34, 35 may include at least one pair of corresponding case contacts 42 which form a completed circuit upon formation of the completed side walls 41. As will be discussed in more detail below, the completed circuit(s) created by case contacts 42 may be monitored by CPU 20 such that a warning or other security feature may be initiated should the circuit(s) become severed, such as during an attempt to pry open case 32, which would be considered a catastrophic event. While shown and described as case contacts on respective side walls of front and back panels 34, 35, it should be understood by those skilled in the art that any suitable circuit configuration may be used so long as the circuit is interrupted when front panel 34 and back panel 35 become partially or completely separated from one another so as to generate the warning or other security feature. Such circuit configurations should be interpreted as within the scope of the present invention. To that end, medication dispensing device 18 may further include one or more of video camera 44, microphone 46 and speaker 48. Speaker 48 may be activated using an amplifier 49 to issue an audible warning. Additionally and/or alternatively, video camera 44 and/or microphone 46 may be activated so as to record video data and/or audio data, respectively, upon occurrence of a catastrophic event, such as a break in the circuit that is formed by case contacts 42. The objective of recording the video and audio data is to help determine the facts surrounding the occurrence of the catastrophic event. This video and audio data can then be transmitted 37 to remote monitoring server 28 by way of a wireless receiver/transceiver (R/T) 50 for review and evaluation by the owner of device 18 or additional parties 31. Furthermore, GPS node 40 may provide information regarding the location of device 18 should a warning/security breach take place when case contacts 42 are compromised. GPS node 40 may be either an active node continually transmitting 37 its location at predetermined time intervals or may be a passive node which will transmit 37 its location after being "pinged" automatically by remote monitoring server 28 or manually by additional party 31. The video, audio and/or GPS data may then be forward to additional party 31, such as a law enforcement entity, (see FIG. 2) if police action is indicated by such data.

A dosage 52 of medication 54 is dispensed by medication dispensing device 18 to a patient only upon the receipt of a valid dose request, wherein the valid dose request must comply with the prescription/dosage data in accordance with prescription 12. A dose request may be initiated by activation of a patient authentication device 56. Patient authentication device 56 may be a biometric sensor such as, but not limited to, one or more of a fingerprint scanner, facial recognition device, retinal scanner, voice recognition or similar system.

Medication dispensing device 18 may also include a touchscreen display 58. Touchscreen display 58 may only be activated upon proper authentication via patient authentication device 56, or may become activated upon a failed authentication wherein touchscreen display 58 is used to receive an optional access code override (such as via a touchscreen keypad and associated passcode as is known in the art). The access code override may be any type of access code, such as an alpha-numeric access code. If the authentication attempt is invalid (i.e., the entered biometric or access code does not match an authorized stored biometric or access code stored in memory), touchscreen display 58 will display an error and request that the user re-authenticate using patient authenticate device 56 or input of the optional code override. After a set number of authentication attempts and/or code attempts, the system will timeout for a preset period of time and report the event to remote monitoring server 28 via WiFi, SMS, or similar wireless communication using R/T 50. If failed attempts continue, CPU 20 will interpret these attempts as a catastrophic event such that camera 44 and microphone 46 may be activated to transmit video and audio data to remote monitoring server 28 and GPS node 40 may be "pinged" as described above.

If "emergency doses" have been prescribed (i.e., doses in addition to those regularly scheduled as per prescription 12), a patient may selectively access an emergency dose contained within medication dispensing device 18 at any time until all emergency doses have been consumed. Using an emergency dose will record an event in a data file stored in the memory of CPU 20, and if desired upload the event to remote monitoring server 28, pharmacist computing system 16 and/or physician computing system 14. Otherwise, dosing times will be restricted to those programmed into the memory of CPU 20 as described above. An upcoming dosing interval (e.g., every 6 hours plus or minus 15 to 30 minutes) will trigger an alert through speaker 48, with programmed repeated alerts given during the dosing interval. The patient can request a dose at any time during this interval. If the interval passes without a dose request, this will be recorded on the data file in the memory of CPU 20.

Touchscreen display 58 may also allow for additional functionality such as displaying information regarding the medication dispensing device (e.g., serial number, service number, etc.), prescribed medication (e.g., medication name, side effects, compatibilities, incompatibilities, etc.), prescription data (e.g., number and timing of dosages, etc.), dosage data (e.g., time of last dosage, time of next available dosage, number of emergency doses remaining, etc.), prescription compliance and the like. In accordance with an embodiment of the present invention, CPU 20 and its associated memory may also include a videoconferencing program application, such as SKYPE or FACETIME, which may be initiated by the patient wherein the touchscreen display 58, video camera 44, microphone 46 and speaker 48 enable remote videoconferencing between the patient and the physician and/or the pharmacist and/or third party vendor personnel associated with remote monitoring server 28 should the patient have any questions or concerns regarding the medication, its dosage or medication dispensing device 18. In accordance with a further embodiment of the present invention, the code override may be remotely utilized by third party vendor associated with remote monitoring server 28 such as for system maintenance/trouble shooting or by an additional party 31 (e.g., law enforcement) such as to gain access to the prescription/dosage data stored within the memory of CPU 20.

In order to dispense dosage 52 upon receipt of a valid request, case 32 including a medication delivery system for holding the medication and delivering the dose to the patient, wherein the medication delivery system includes a medication holding area 60 and a dosage holding area 62. The system further includes a first gate 64 is located at an entry end dosage holding area 62 of between medication holding area 60 and dosage holding area 62 and is operable (such as by way of a first actuator 66) to selectively open and thereby allow an individual dosage 52 of medication 54 housed in medication holding area 60 to enter dosage holding area 62. The system further includes a second gate 68 is located at a dispending end at the opposing end of dosage holding area 62 and prevents release of dosage 52 until second gate 68 is selectively opened (such as by way of a second actuator 70). To facilitate movement of the medication/individual dosage through medication dispensing device 18, a vibrating motor 72 is associated with the medication holding area 60 and is energized when dosage 52 is being dispensed. The vibration of motor 72 serves to jostle medication 54 until individual dosage 52 is immediately adjacent the opening created by opened first gate 64 and in the proper orientation so as to enter dosage holding area 62. In accordance with an aspect of the present invention, first and second actuators 66, 70 are servomotors 73 where, at most, only one servomotor 73 is operable at a time so that first or second gates 64, 68 are never both in an open position at the same time.

In accordance with a further aspect of the present invention, a photogate 74 is associated with dosage holding area 62 wherein photogate 74 regulates activation of actuators 66, 70. For instance, first actuator 66 may be powered so as to open first gate 64 wherein dosage 52 exits medication holding area 60 and enters dosage holding area 62. Dosage 52 interrupts photogate 74 such that first actuator 66 is returned to its original state and first gate 64 is closed. Second actuator 70 can then be powered to open second gate 68 and thereby allow dosage 52 to exit the dosage holding area 65. Once photogate 74 is no longer impeded by dosage 52, second actuator 70 can then return to its original state thereby closing second gate 68. In this manner, release of medication may be controlled so as to limit distribution of medication 54 to a single dosage 52 per valid request.

Case 32 may be configured so as to be substantially waterproof. To help ensure waterproofing of the interior components of device 18, medication dispensing device 18 may further define a dosage retrieval area 76 located after second gate 68. Case 32 includes a retrieval shutter 78 operable to selectively open once dosage 52 enters the dosage retrieval area 76 and second gate 68 is closed by second actuator 70. Retrieval shutter 78 is sealed within case 32 by a watertight gasket along the inner and/or outer edges of retrieval shutter 78. Retrieval shutter 78 is configured to slidably engage case 32 wherein retrieval shutter 78 slides open to allow passage of dosage 52. To secure retrieval shutter 78 in a closed position when a dosage is not being removed, case 32 carries a retrieval shutter locking pin 80 that engages retrieval shutter 78 to prevent unwanted or unauthorized sliding of the shutter. Retrieval shutter locking pin 80 may be retracted upon command from CPU 20 such that retrieval shutter 78 can open and dosage 52 be removed. When retrieval shutter 78 is opened, a time stamp will be recorded in the data file and associated with this event. If retrieval shutter 78 has not been closed satisfactorily in certain period of time, the device will continuously sound a warning through speaker 48 and/or touchscreen display 58. After a second period of time, an alarm may be sent to remote monitoring server 28 notifying the third party vendor of the retrieval shutter's malfunction so that proper corrective action may be readily employed.

Figure 5:
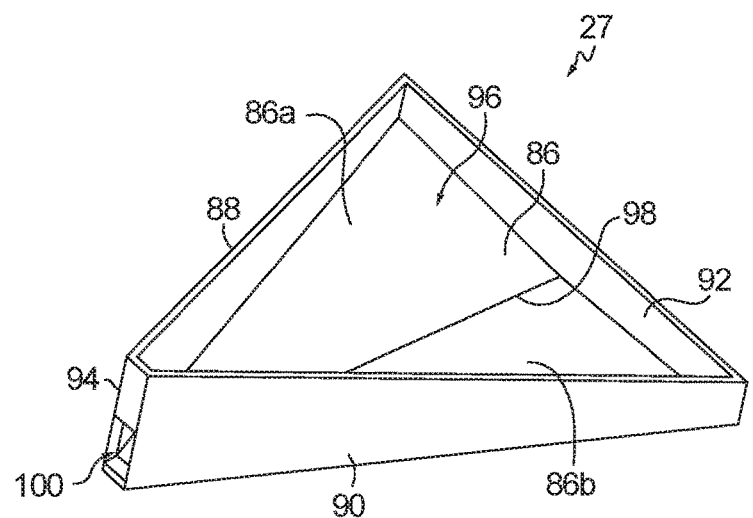
FIG. 5 is an embodiment of a prescription drug tray configured to be used in conjunction with the medication dispensing device shown in FIGS. 3A-3C.

As best seen in FIG. 5, medication 54 may be loaded into medication dispensing device 18 via a tray 27. As described above, tray 27 may be manually loaded by the pharmacist or may be loaded via medication filling device 24. In either case, once tray 27 has been filled with the proper type and number of medication 54, tray 27 is inserted into medication holding area 60. To facilitate insertion of tray 27, case 32 is configured to include a tray shutter 82 configured to allow passage of tray 27 therethrough. Similar to retrieval shutter 78 described above, tray shutter 82 is slidably sealed within case 32 by a watertight gasket along the inner and/or outer edges of tray shutter 82 wherein tray shutter 82 slides open to allow passage of tray 27. To secure tray shutter 82 in a closed position when tray 27 is not being inserted or removed, case 32 carries a tray shutter locking pin 84 that engages tray shutter 82 to prevent unwanted or unauthorized sliding of tray shutter 82. Pin 84 may be retracted upon command from CPU 20 such that tray shutter 82 can open and tray 27 can be inserted or removed.

Tray 27 includes a bottom 86 with upwardly extending side walls 88, 90, rear wall 92 and front wall 94 defining a tray interior 96. Each of side walls 88, 90 form an acute angle with rear wall 92 such that rear wall 92 has a greater length than front wall 94. Additionally, each of side walls 88, 90 also increase in width as they extend from rear wall 92 toward front wall 94 such that rear wall 92 has a smaller width than front wall 94. Bottom 86 may also include a central valley 98 such that bottom halves 86a and 86b are sloped as they extend from central valley 98 to side walls 88, 90, respectively.

Tray 27 is proportioned so as to substantially occupy medication holding area 60 defined by case 32. That is, side walls 88, 90 of tray 27 are configured to lie against medication holding area side walls 60a, 60b, respectively, such that little to no gap is formed between tray 27 and medication holding area side walls 60a, 60b. Tray side walls 88, 90 are of such length that rear wall 92 lies against tray shutter 82 while front wall 94 abuts first gate 64 when tray 27 is loaded into medication dispensing device 18. Front wall 94 is configured to define an opening 100 proportioned to allow individual dosage 52 (see FIG. 3B) to pass from tray interior 96 through first gate 64 into dosage holding area 62. The internal surface of case front panel 34 is configured to seat against the top edges of walls 88, 90, 92, 94 so as to prevent ejection of medication 54 from tray 27 should medication dispensing device 18 be inverted after tray 27 is loaded into the device. Further, the interior surface of the bottom panel of case 32 includes a ramp portion or other retaining feature so as to hold the top edge of rear wall 92 against the inner surface of front panel 34. As a result, tray 27 is pitched such that the portion of tray bottom 86 closest to rear wall 92 is higher than the portion closest to front wall 94. This pitch, combined with the slope created by bottom halves 86a, 86b in conjunction with valley 98, operates to direct medication 54 toward tray front wall 94, opening 100 and first gate 64.

Multiple versions of tray 27 may be fabricated wherein each tray 27 includes a tray opening 100 having a different size. In this manner, a pharmacist can selectively choose a tray 27 for loading wherein tray opening 100 is selected to be slightly larger than medication 54 prescribed. As a result, tray opening 100 effectively throttles the dispensing of individual dosages 52 such that only one pill is distributed into dosage holding area 62 per request.

Figure 6:
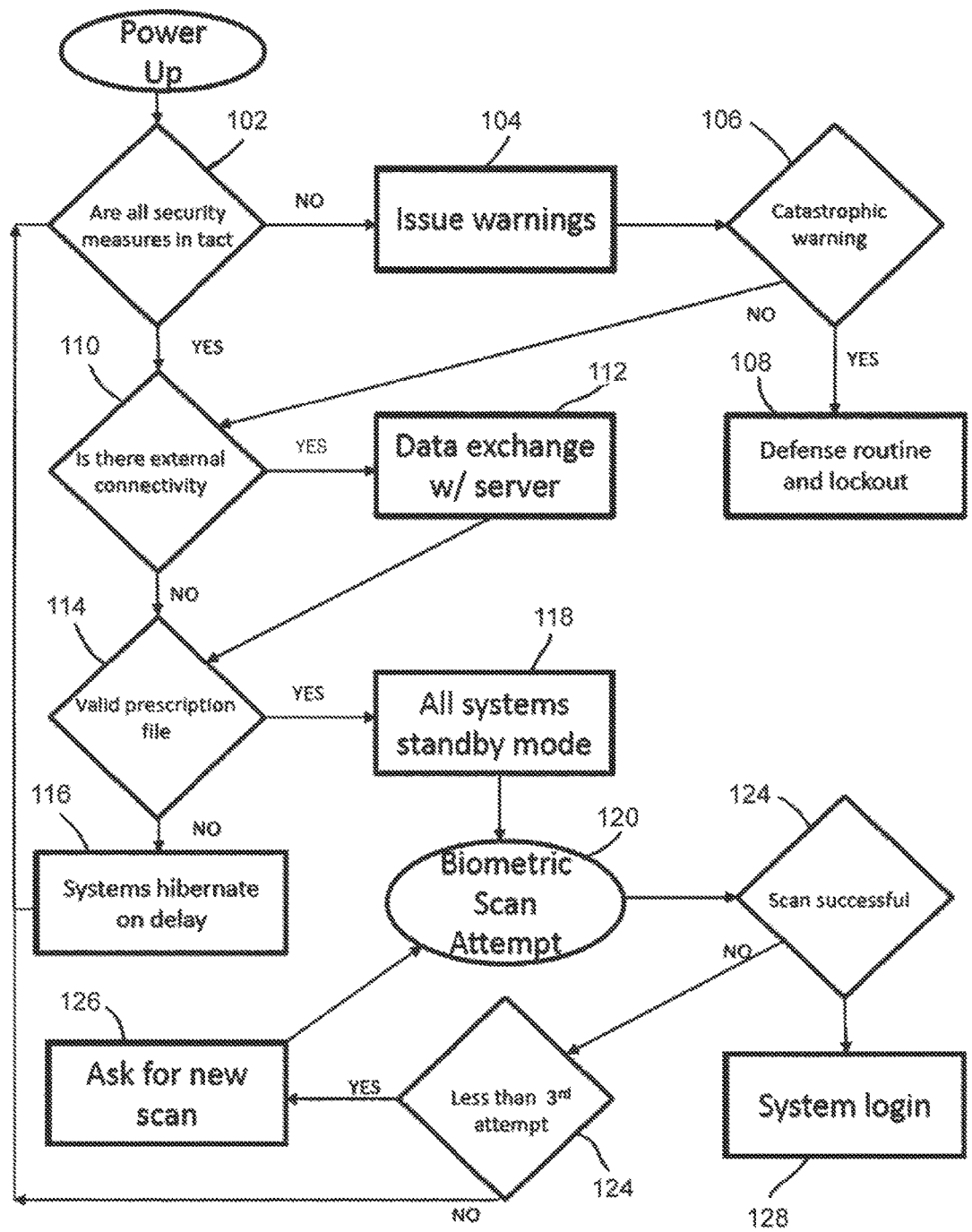
FIG. 6 shows a logic flow diagram for initialization of the medication dispensing device shown in FIGS. 3A-3C.
Figure 7:
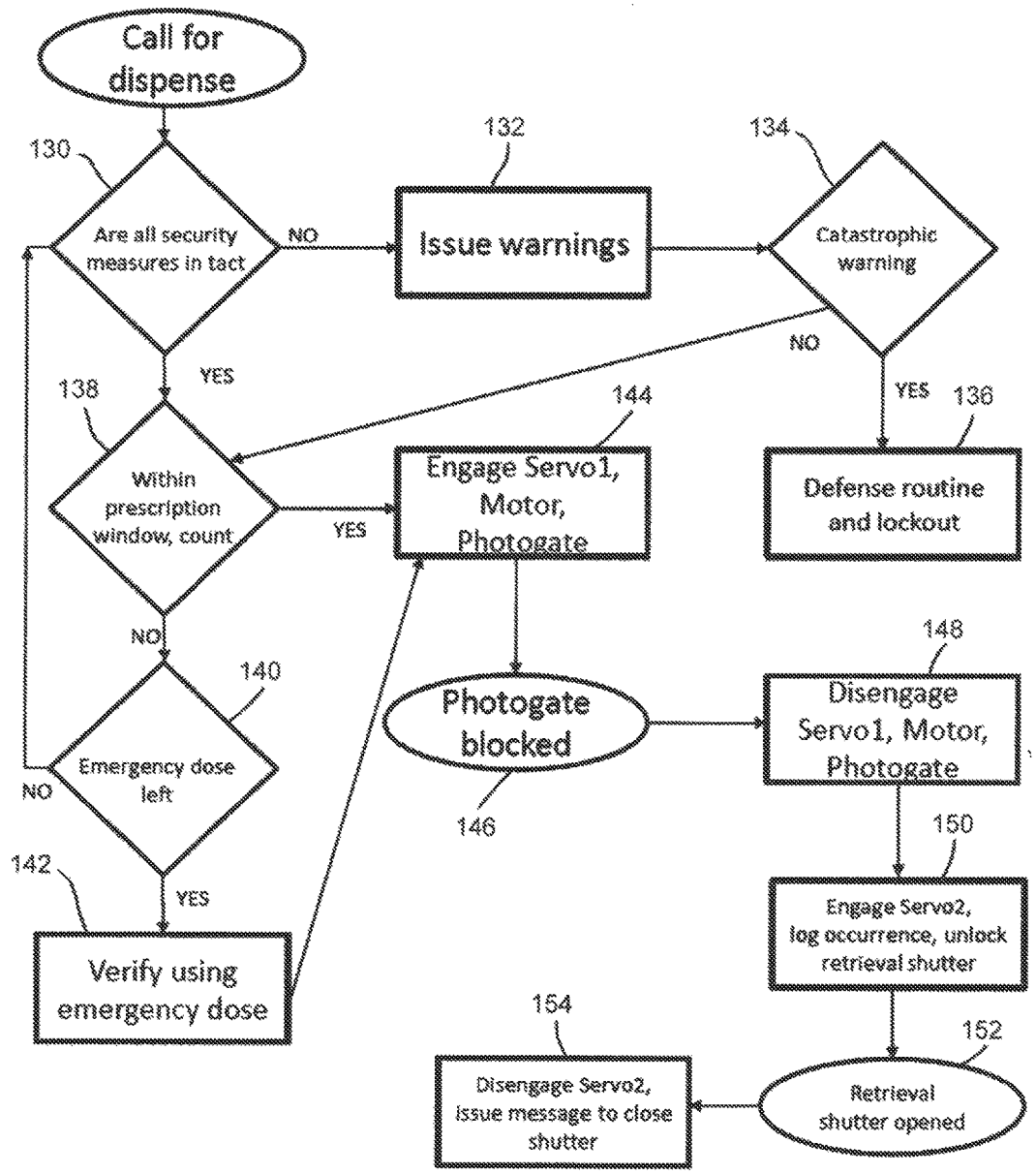
FIG. 7 shows a logic flow diagram for dispensing a medication from the medication dispensing device shown in FIGS. 3A-3C.
Figure 8:
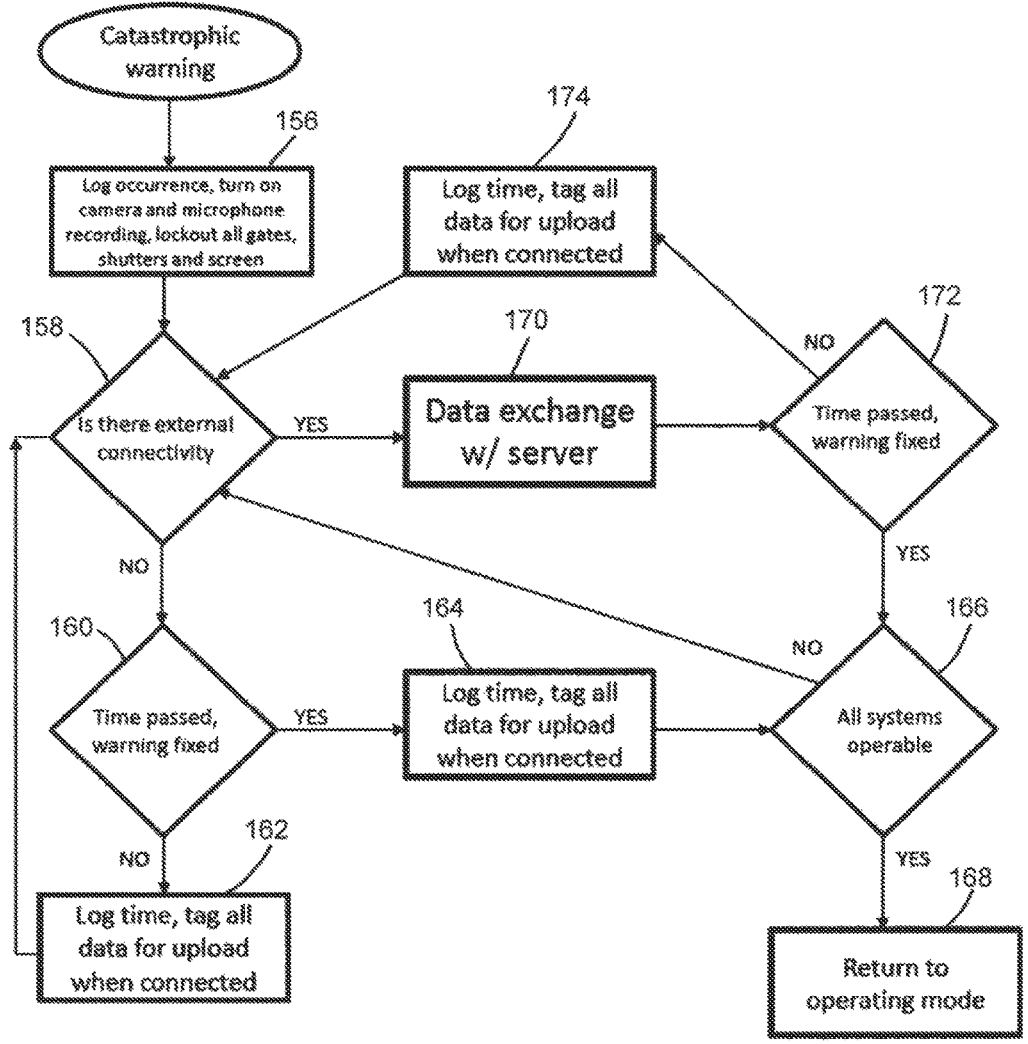
FIG. 8 shows a logic flow diagram for a catastrophic sequence encountered by the medication dispensing device shown in FIGS. 3A-3C.
Figure 9:
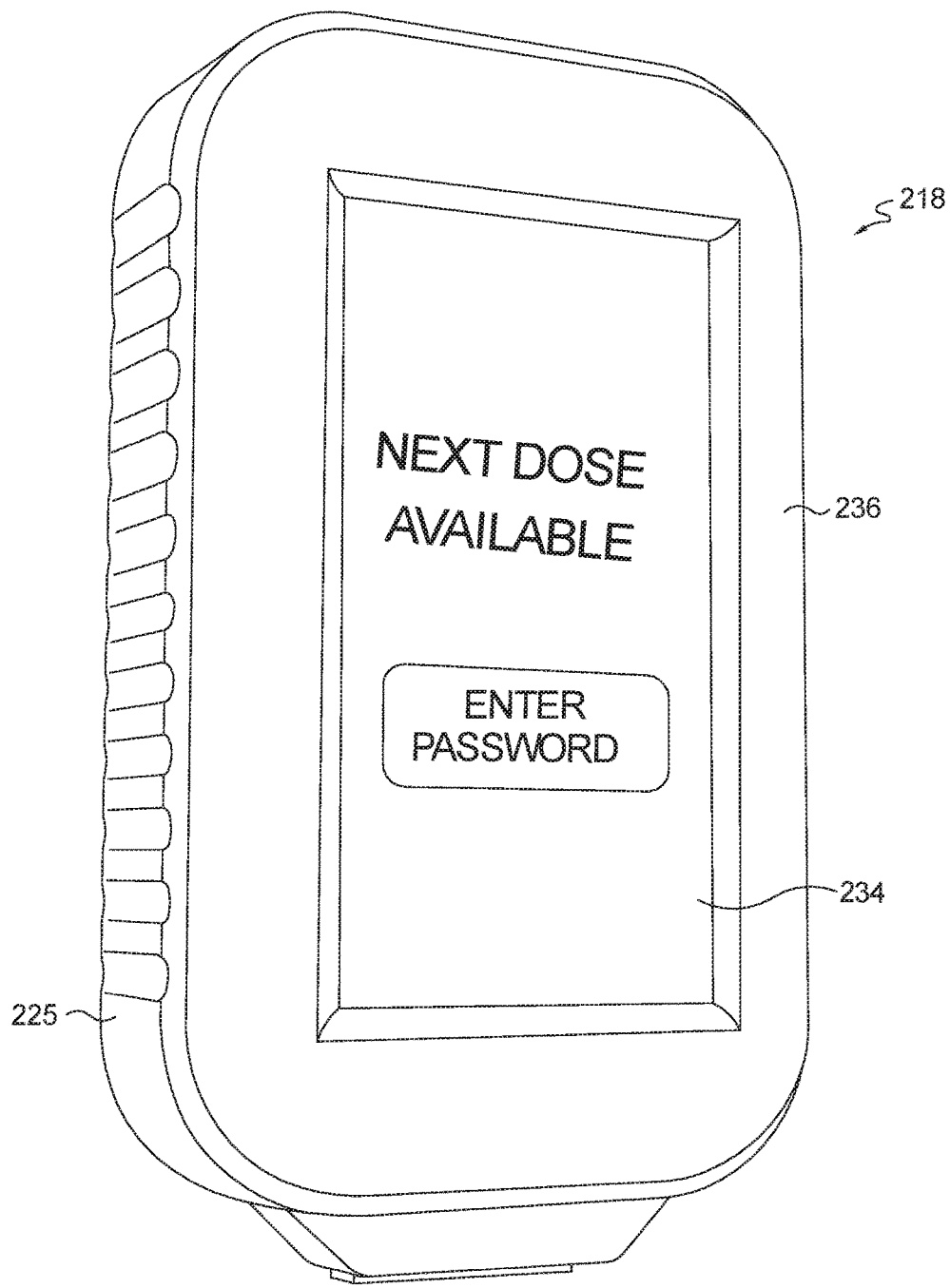
FIG. 9 is a perspective view of an alternative embodiment of a medication dispensing device in accordance with the present invention.
Figure 10:
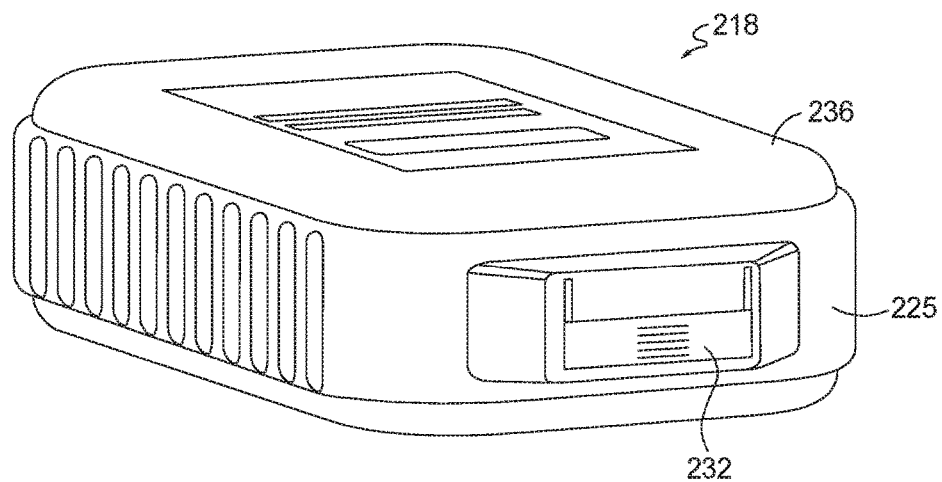
FIG. 10 is an end perspective view of the medication dispensing device shown in FIG. 9 showing the dispensing door in a closed position.
Figure 11:
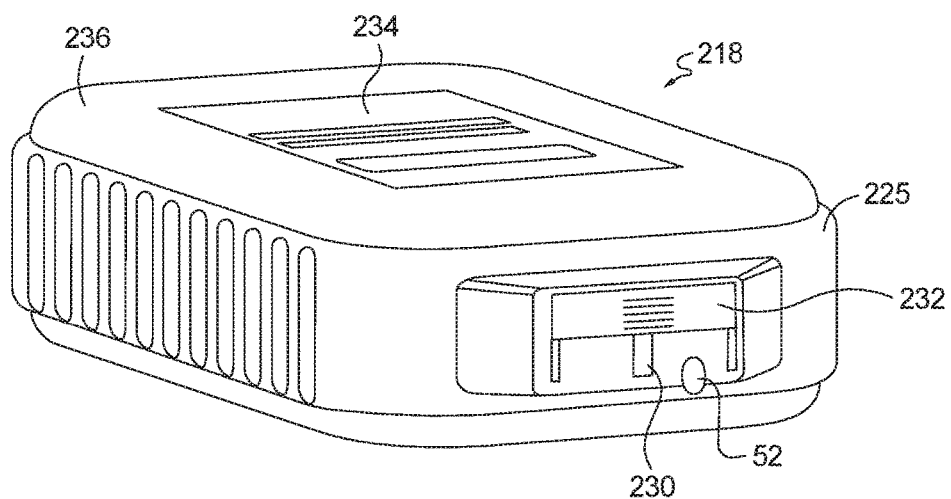
FIG. 11 is an end perspective view of the medication dispensing device shown in FIG. 9 showing the dispensing door in an open position.

FIGS. 6-8 show logic flow diagrams for various actions carried out by medication dispensing device 18. The power-up and initialization protocol is shown in FIG. 6. Initially, at step 102, CPU 20 queries the security measures (i.e., case contacts 42, actuators 66, 70) to verify that all measures are intact and operating. If the measures are not intact, a warning is issued (such as an auditory warning via speaker 48) at step 104. Following the warning, CPU 20 determines whether the warning is a catastrophic warning at step 106 requiring initiation of the defense routine and device lockdown (see FIG. 8) at step 108. Alternatively, at step 110, if the security measures are intact or if the warning is not a catastrophic warning, CPU 20 queries receiver/transceiver (R/T) 50 to determine if there is external wireless connectivity. If there is wireless connectivity, R/T 50 conducts a data exchange with physician computing system 14, the pharmacy computing system 16 and/or the data server of remote monitoring server 28 at step 112.

Following the data exchange, or should no wireless connectivity be detected, CPU 20 then interrogates the memory of CPU 20 to determine if there is a valid prescription file stored in memory at step 114. At step 116, if there is no valid prescription file, medication dispensing device 18 enters hibernation mode until another power-up sequence is initiated. If a valid prescription 12 is on file, medication dispensing device 18 enters stand-by mode awaiting a dose request from the patient at step 118. The device exits stand-by mode upon a dose request, such as through activation of patient authorization device 56 (i.e., the biometric sensor) at step 120. If the biometric scan is successful, touchscreen display 58 is activated and the patient can request a dosage at step 122. If the biometric scan is unsuccessful at step 124, a warning is issued and the patient is prompted to attempt a new scan at step 126. If there are a preselected number of unsuccessful scans (e.g., 3 unsuccessful scans) CPU 20 reinitiates the power-up protocol and queries the device's security measures as discussed above at step 128.

Turning now to FIG. 7, displayed is a logic flow diagram to determine if a dosage may be dispensed upon a patient request (i.e. whether the request is a valid request). Prior to dispensing a dosage, CPU 20 queries the security measures to verify that they are intact at step 130 (as discussed above). If the security measures are not intact, a warning is issued at step 132 and CPU 20 determines whether the warning constitutes a catastrophic warning at step 134 necessitating initiation of device's 18 defense routine and device lockout (see FIG. 8) at step 136. If the security measures are intact or if the warning is not a catastrophic warning, CPU 20 interrogates the data file stored in its memory to determine whether the request is within an authorized prescription window at step 138. If the request is not within an authorized prescription window, CPU 20 interrogates the data file to determine whether any emergency doses are available at step 140. If no emergency doses are available, CPU 20 reinitiates the dispense routine.

If the request is within an authorized prescription window, of if an emergency dosage is available (step 142), CPU 20 initiates engagement of first actuator 66, motor 72 and photogate 74 at step 144 so as to direct an individual dosage 52 from medication holding area 60/tray 27 into dosage holding area 62 as described above. Upon passage of dosage 52 into dosage holding area 62, photogate 74 is blocked/interrupted at step 146 wherein photogate 74 sends a signal to CPU 20 of its state change. CPU 20 then disengages first actuator 66 so as to close first gate 64, deactivates motor 72 and photogate 74 at step 148. Once first gate 64 is closed, CPU 20 sends a command to engage second actuator 70 and logs the occurrence of the dosage dispensing in the data file at step 150. If case 32 includes a retrieval shutter 78, CPU 20 issues a command to retrieval shutter locking pin 80 to retract and thereby allow retrieval shutter 78 to open and dispense dosage 52 to the patient at step 152. At step 154, CPU 20 then disengages second actuator 70 thereby closing second gate 68 and issues a command to close retrieval shutter 78 and extend retrieval shutter locking pin 80.

FIG. 8 shows a logic flow diagram for a catastrophic warning. If a warning is determined to constitute a catastrophic warning (see above), CPU 20 generates a data log of the occurrence and activates camera 44 and microphone 46 to record video and audio data at step 156. CPU 20 also locks all gates, shutters, servomotors and the touchscreen display. CPU 20 then determines whether there is external connectivity via R/T 50 at step 158. At step 160, if there is no connectivity and the warning has not been fixed, CPU 20 logs the time and tags all data (i.e., camera and microphone recordings) for upload once external connectivity is established at step 162. If there is no connectivity and the warning has been fixed, CPU 20 still logs the time and tags all data for upload once external connectivity is established at step 164, but also attempts to place all systems in normal operating condition. If all systems are operable at step 166, the device is returned to normal operation at step 168. However, is all systems are not operable, CPU 20 determines whether there is external connectivity so as to exchange the catastrophic warning data collected.

On the other hand, if there is external connectivity, the data (i.e., camera and microphone recordings) is exchanged with an external server at step 170, such as remote monitoring server 28. CPU 20 then determines whether the warning has been fixed at step 172. If the warning has not been fixed, CPU 20 logs the event and camera 44 and microphone 46 continue to record video and audio data. This data is then exchanged with remote monitoring server 28 or tagged for later upload should external connectivity have been lost at step 174. However, if the warning has been fixed, CPU 20 attempts to place all systems in normal operating condition. If all systems are operable, the medication dispensing device 18 is returned to normal operation. If all systems are not operable, CPU 20 determines whether there is external connectivity so as to continue to exchange the catastrophic warning data being collected, such as by camera 44, microphone 46 and/or GPS node 40.

Turning now to FIGS. 9-19, an additional embodiment of a medication dispensing device in accordance with the present invention is generally indicated by reference numeral 218. Medication dispensing device 218 generally includes a cartridge housing 220 having an upwardly extending sidewall 222 removably secured to a downwardly extending sidewall 224 of a main housing 226. In certain embodiments, sidewalls 222/224 may include one or more pairs of opposing case contacts so as to verify device integrity as described above with regard to device 18. Should anybody attempt to tamper with device 218, the case contacts will become disrupted such that a trigger signal may be initiated as discussed above, and as further discussed below. An optional rubber guard 225 may encircle part or all of sidewalls 222/224 when cartridge housing 220 is coupled with main housing 226. In accordance with an aspect of the present invention, a portion of sidewalls 222/224 may be configured to include an extended lobe 222a/224a whose external edge 228 defines the terminus of a dispensing channel 230. Rubber guard 225 does not overlap lobe portion 222a/224a such that a door 232 may selectively open and close channel 230.

Figure 16:
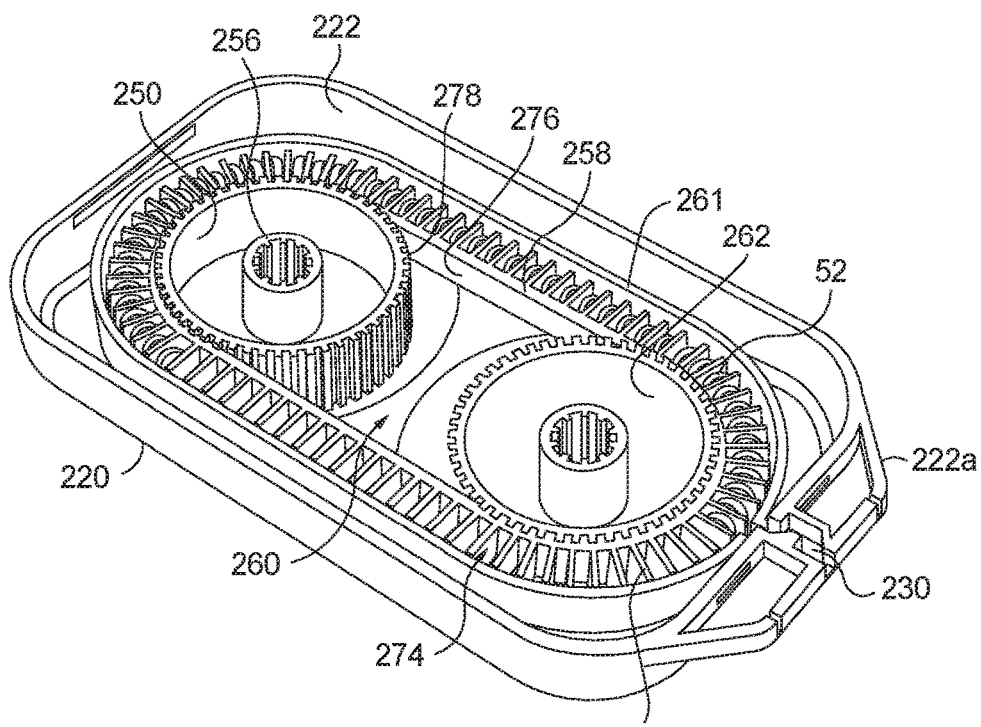
FIG. 16 is a side perspective view of the cartridge housing of the medication dispensing device shown in FIG. 9 with the cartridge cover removed.
Figure 17:
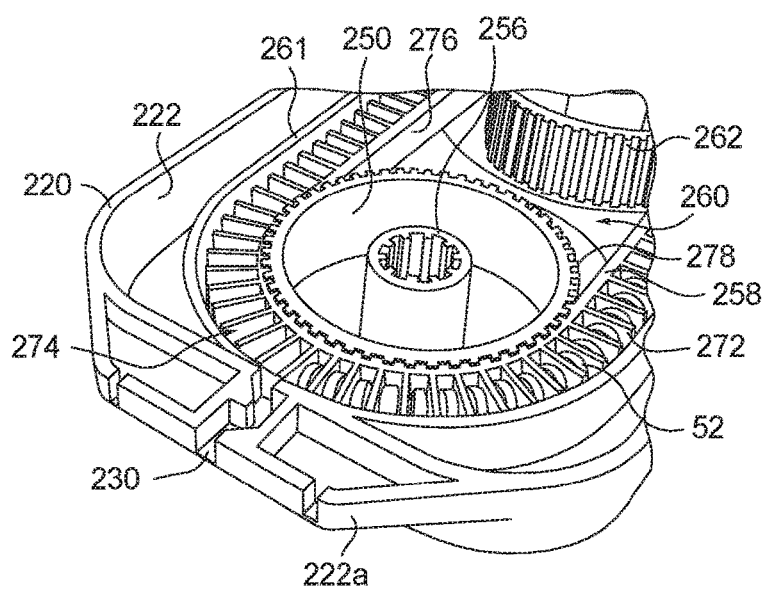
FIG. 17 is a detailed view of the dispensing channel of the cartridge housing of the medication dispensing device shown in FIG. 9.
Figure 18:
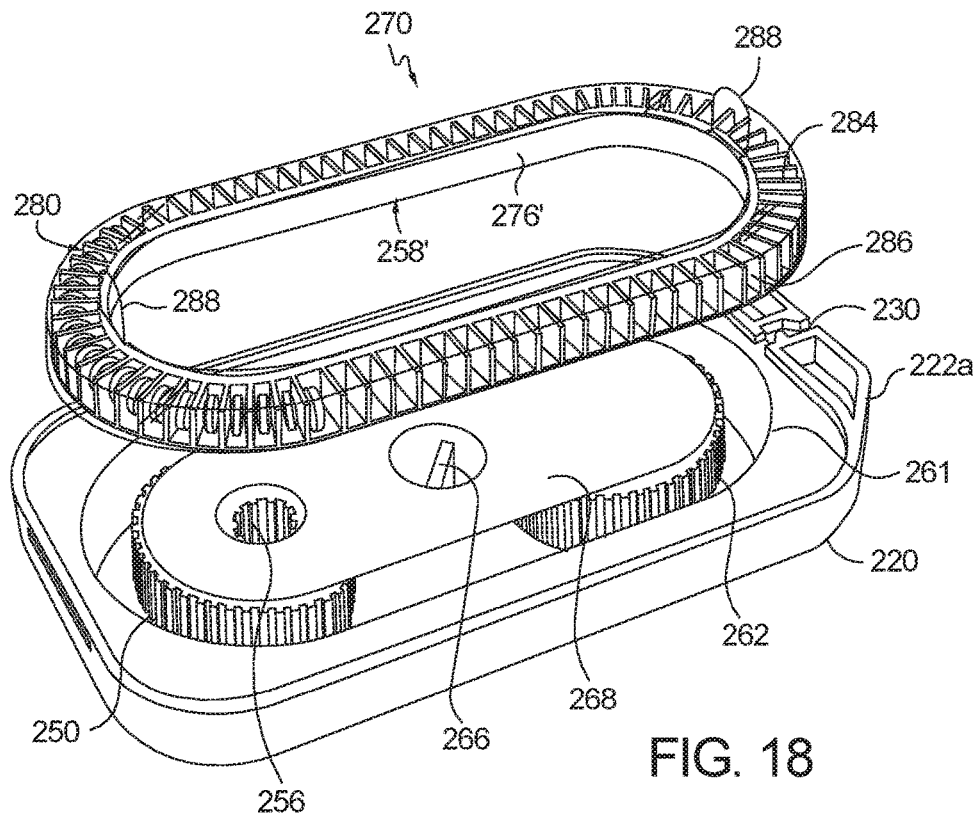
FIG. 18 is a side perspective view of the cartridge housing of the medication dispensing device shown in FIG. 9 with a replaceable cartridge in an unloaded position.
Figure 19:
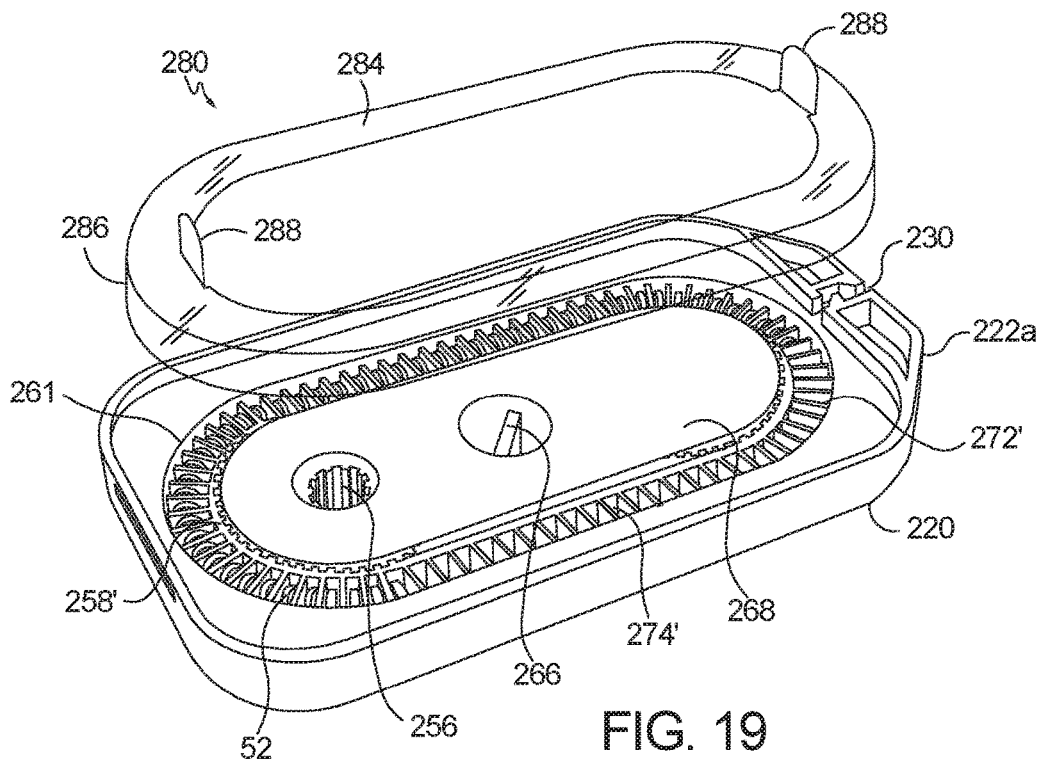
FIG. 19 is a side perspective view of the cartridge housing of the medication dispensing device shown in FIG. 9 with a replaceable cartridge in a loaded position.

As seen most clearly in FIGS. 16 and 17, lobe 222a (and 224a, not shown) defines an extended channel 230 through which a dosage 52 must pass when being dispensed. Channel 230 may be proportioned so as to allow only a single dosage to pass through the channel at a time, and such proportions may be varied as needed depending upon the size and shape of the prescribed medication. In accordance with an aspect of the present invention, channel 230 may be configured to have a non-linear profile such that dosage 52 must traverse a tortuous path before exiting device 218. Non-linear channel 230 may assist in preventing unauthorized dispensing of a dosage as any tool inserted within non-linear channel 218 in an attempt to dislodge an authorized dosage will become obstructed by one or more walls of channel 218.

Returning now to FIGS. 9-12, medication dispensing device 218 may also include a mobile computing device, such as, for example, a smartphone 234. Smartphone 234 may be secured to main housing 226 by a front cover 236. In accordance with an aspect of the embodiment of device 218, smartphone 234 may be utilized so as to harness its inherent memory and computing power, and may replace one or more of the functionalities and modalities described above with regard to device 18, namely CPU 20, GPS module 40, camera 44, microphone 46, speaker 48, amplifier 49, patient authentication device 56 and touchscreen 58. Thus, it should be understood by those skilled in the art that medication dispensing device 218 may include individual components such as those described above with regard to device 18, but instead utilizes smartphone 234 to provide similar features and functionalities.

Figure 13:
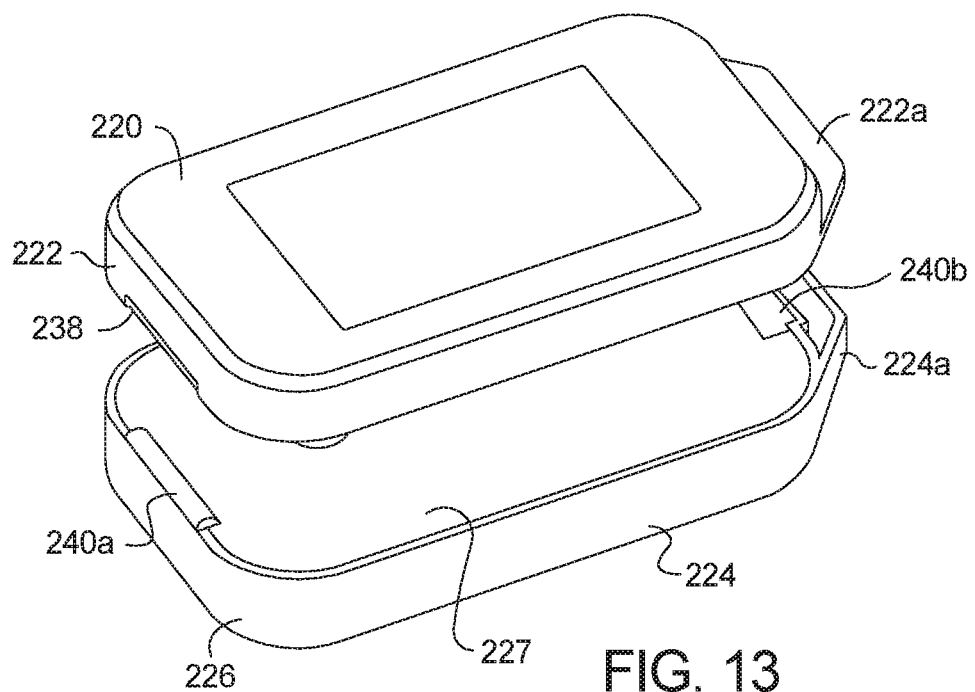
FIG. 13 is a side perspective view of the housing members of the medication dispensing device shown in FIG. 9 in a decoupled position.
Figure 14A:
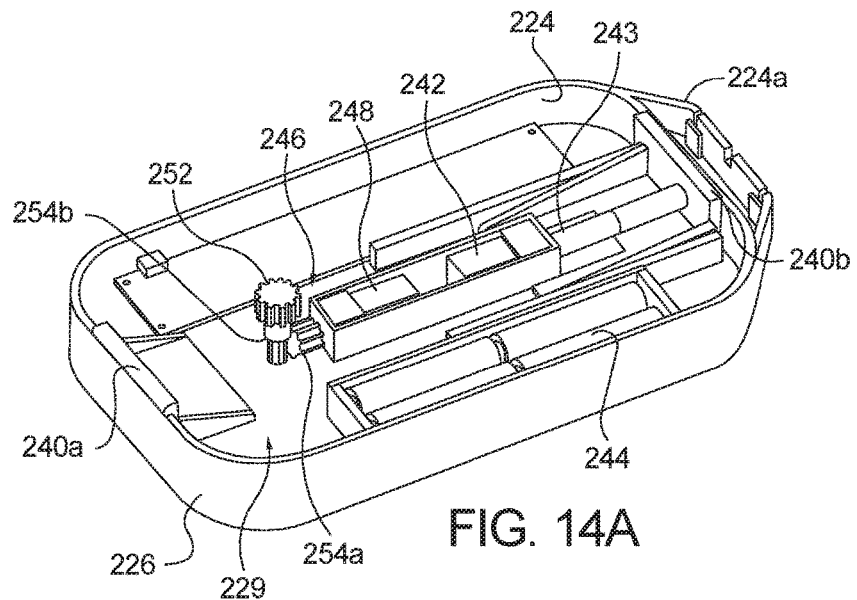
FIG. 14A is a side perspective view of the main housing of the medication dispensing device shown in FIG. 9 showing the locking tab in the extended position.
Figure 14B:
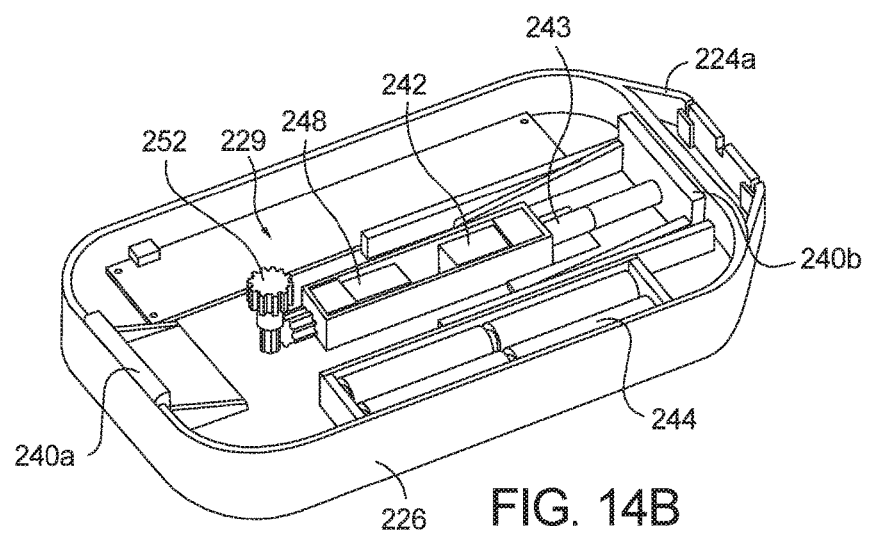
FIG. 14B is a side perspective view of the main housing of the medication dispensing device shown in FIG. 9 showing the locking tab in the retracted position.

Turning now to FIG. 13, in accordance with an aspect of the present invention, cartridge housing 220 is configured for removable attachment to main housing 226, such as through one or more corresponding slots and tabs. Cartridge housing 220 may include one or more slots 238 (only one shown) which are configured to mate with corresponding tabs 240, such as 240a, 240b as shown, so as to secure the two housings 220/226 together. As shown most clearly in FIGS. 14A and 14B, one of tabs 240, such as tab 240b, may be coupled to an actuator member, such as motor 242 via a threaded rotating shaft 243 so as to constitute an example of motor driven locking mechanism in accordance with an aspect of the present invention. Tab 240b may be driven upon powering of motor 242 via battery 244. In this manner, tab 240b may be slidably driven upon shaft 243 between an extended position (as shown in FIG. 14A) whereby tab 240b resides in its respective slot 238 to secure housings 220/226 together, and a retracted position (as shown in FIG. 14B) whereby tab 240b is withdrawn from its slot thereby permitting removal of cartridge housing 220 from main housing 226. In accordance with an aspect of the present invention, motor 242 is only powered upon receipt of a proper authentication input by a device administrator, such as a pharmacist, for example. An authentic input by an administrator may also operate to override any warning issued by the disruption of the case contacts, if provided.

Figure 12:
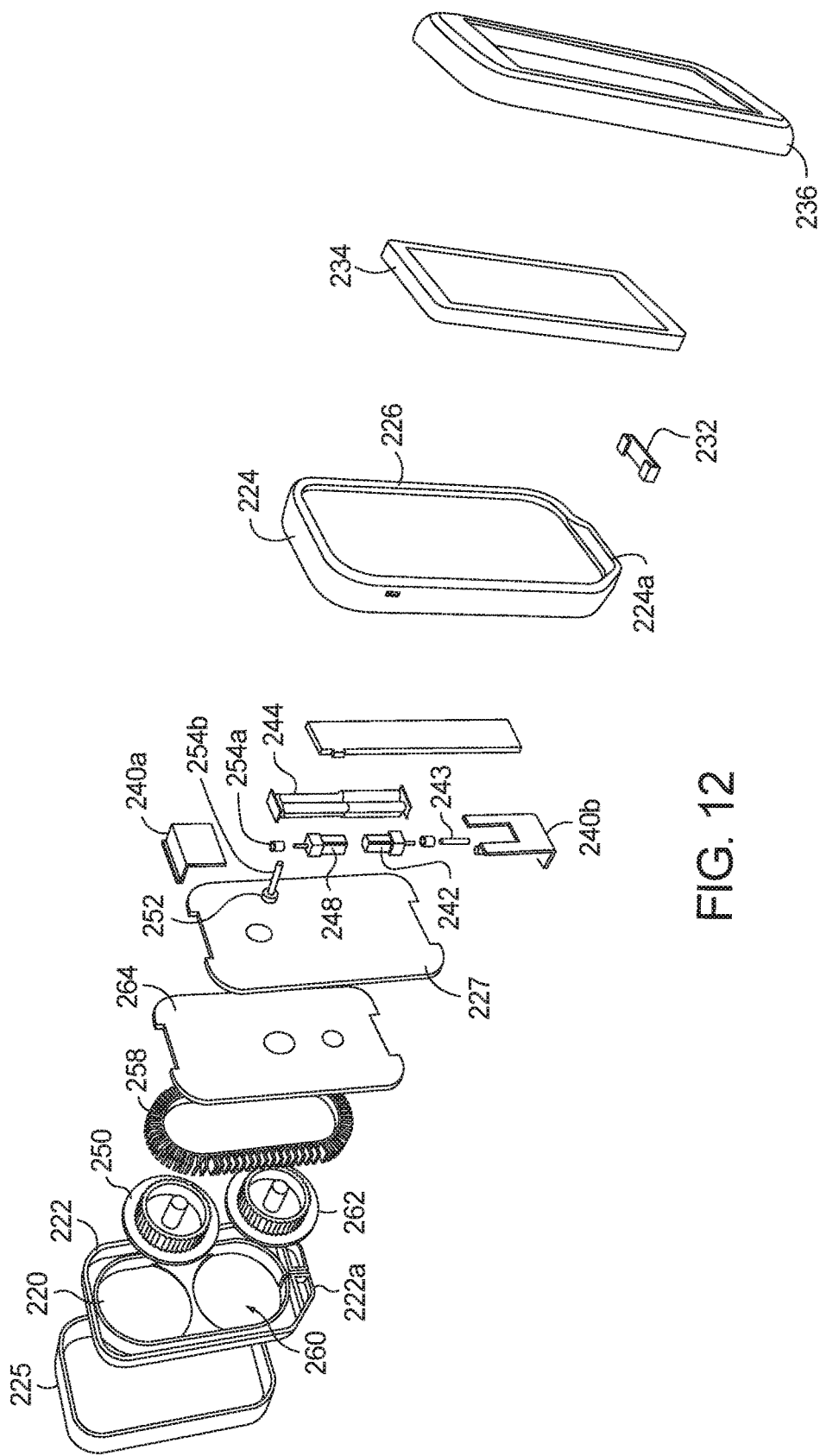
FIG. 12 is an exploded view of the medication dispensing device shown in FIG. 9.

As further shown in FIGS. 12, 14A and 14B, main housing 226 may further define a controller receiving area 229 that may include a driver member 246 and associated actuator (drive motor) 248. Driver member 246 is coupled to a driven member 250, such as a pulley, in cartridge housing 220 as will be described in more detail below. By way of example, and by no means limiting specifically thereto, driver member 246 may include a gear 252 extending outwardly from the plane formed by the terminal edge of downwardly extending sidewall 224. To prevent dust or debris from entering main housing 226, a main housing cover 227 may be included. Rotation of driver member 246 and gear 252 may be translated through mating 45 degree miter gears, where a first miter gear 254a is coupled to drive motor 248 and a second miter gear 254b is coupled to driver member 246.

Figure 15:
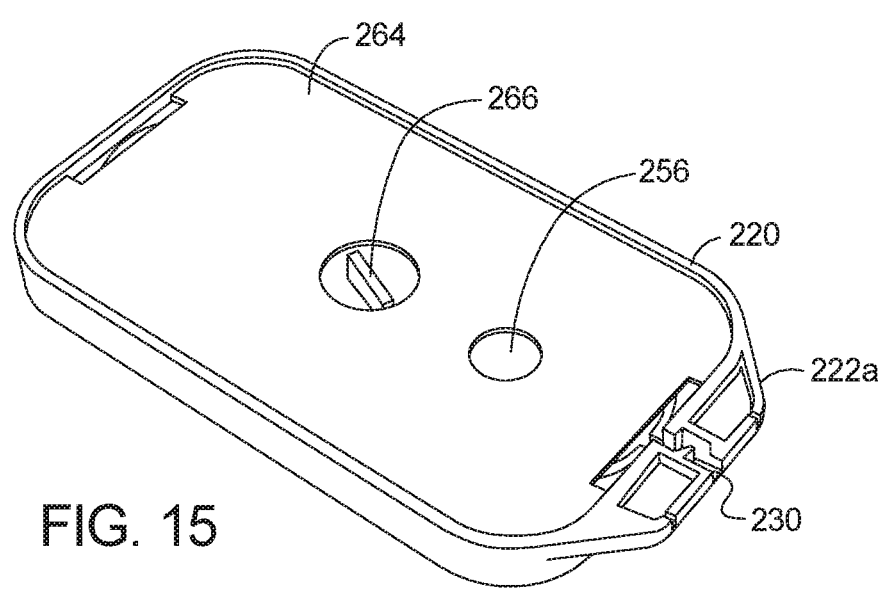
FIG. 15 is a side perspective view of the cartridge housing of the medication dispensing device shown in FIG. 9.

With reference to FIGS. 15-17, gear 252 may be configured to engage pulley shaft 256 on driven member (pulley) 250 residing within cartridge housing 220. Thus, as gear 252 is rotated upon powering of drive motor 248, pulley shaft 256 is caused to rotate such that driven member 250 advances belt 258 within cartridge receiving area 260 defined by cartridge wall 261. Drive motor 248 may only be powered once a valid request for a dosage has been inputted into smartphone 234, similar to that process discussed above with regard to device 18. A passive member (pulley) 262 may be employed to assist advancement of belt 258 as will be discussed in greater detail below. To prevent contamination of cartridge receiving area 260 and any loaded dosages 52 contained therein, cartridge housing 220 may include a cover plate 264 which is selectively removable, such as through a thumb screw 266. An additional pulley cover plate 268 may also be used to prevent contamination (see FIG. 18-19).

As shown in FIGS. 16-19, a belt 258 has a plurality of outwardly extending fingers 272 which define a plurality of dosages slots 274 therebetween. Dosage slots 274 are proportioned to receive a single respective dosage 52 therein. Inner wall 276 of belt 258 is sized to snuggly engage pulley 250/262 so as to enable rotation of belt 258 upon powering of drive motor 248 as discussed above. Pulleys 250/262 and/or inner wall 276 of belt 258 may also be configured to include cogs 278 and/or slots (not shown) to assist rotation of the belt, prevent slipping of the belt and improve indexing of the belt with respect to dispensing slot 230. That is, drive motor 248 may be indexed to power rotation of driver member 246 so as to advance belt 258 only that distance required to align a next sequential dosage 52 with dispensing slot 230. Proper indexing ensures that only a single dosage is dispensed upon receipt of a valid request as discussed above with regard to embodiment 18.

In accordance with an aspect of the embodiment of medication dispensing device 218, belt 258 may be configured to remain within cartridge receiving area 260 while dosages 52 are individually added to respective dosage slots 274 when device 218 is being loaded. In a further aspect, such as that shown in FIGS. 18 and 19, medication dispensing device 218 may include a cartridge 270 comprising belt 258' and cartridge cover 280. Belt 258' is similar to belt 258 but is configured to include a floor 282 integrally formed with belt inner wall 276' and outwardly extending fingers 272'. Cover 280 includes a top panel 284 and outer sidewall 286. Cover 280 is proportioned so as to snuggly fit upon belt 258' such that dosages 52 cannot fall out of dosage slots 274' when the cover is in place. In this manner, cartridge 270 may be loaded within cartridge receiving area 260 such that belt 258' fits snuggly upon pulleys 250/262 as described above. Cover 280 may then be removed from cartridge 270 via one or more cartridge tabs 288. Dosages 52 will then be retained within their respective dosage slots 274' via fingers 272' of the belt and cartridge cover 264 and cartridge wall 261 of the cartridge housing 220.

Figure 20:
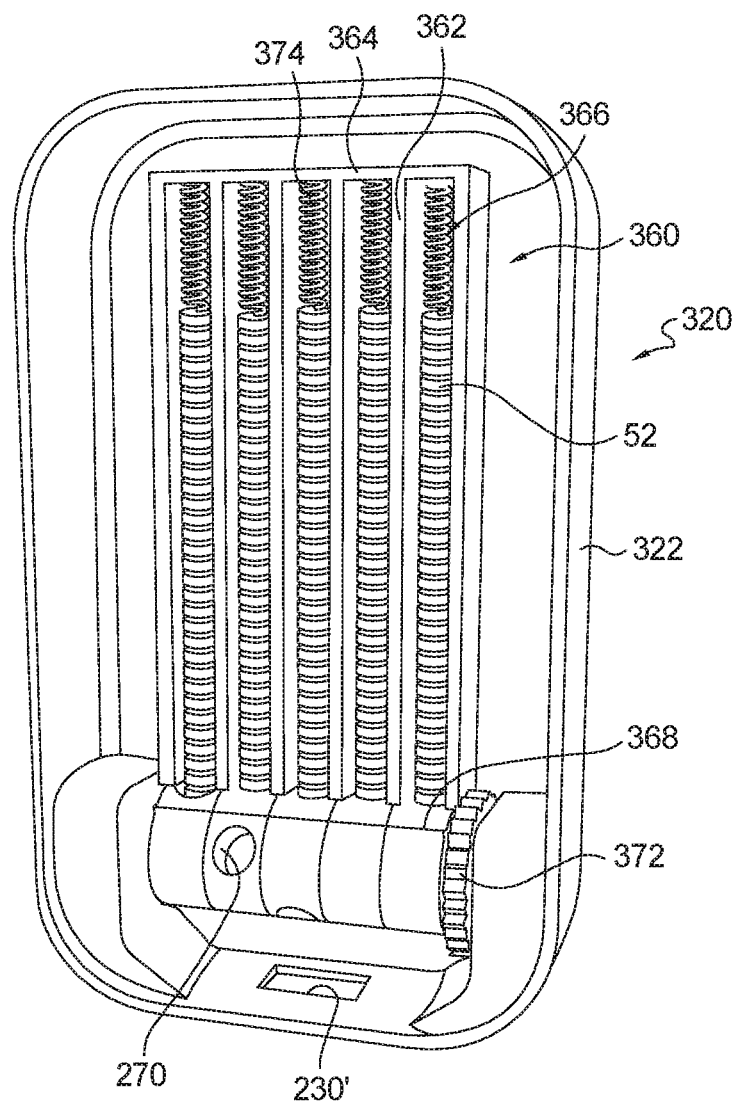
FIG. 20 is a perspective view of an alternative embodiment of a cartridge for use within a medication dispensing device in accordance with the present invention.

Turning now to FIG. 20, a further embodiment of a medication dispensing device 218 may replace cartridge housing 220 with cartridge housing 320. Cartridge housing 320 includes an upwardly extending sidewall 322 configured to mate with downwardly extending sidewall 224 of main housing 226 as described above. As shown in FIG. 20, cartridge housing 320 may be configured not to include an extended lobe as described above. Main housing 226 would likewise be configured so as not to include an extended lobe 224a. However, for improved security, an extended lobe portion, and non-linear dispensing channel, may be included if desired.

Cartridge housing 320 includes a cartridge receiving area 360 which includes a plurality of walls 362 arranged in spaced parallel relation with one another. A back wall 364 extends across the rear end of walls 362 so as to define a number of dispensing channels 366. By way of example, cartridge 320 is shown to include five dispensing channels 366, although it should be understood by those skilled in the art that any number of channels may be included. The opposing, forward edge of walls 362 terminate at a plurality of dispensing wheels array, wherein each dispensing channel 366 terminates at a dedicated dispensing wheel 368. Each dispensing wheel 368 includes a recess 370 which is proportioned to receive a single dosage 52 from a stack of dosages loaded within the dispensing channels. Recesses 370 may be rotationally offset from one another a common number of degrees, such that the sum of the total number of degrees equals 360. By way of example, cartridge 320 having five dispensing channels would have five associated dispensing wheels. As a result, each recess 370 would have its center offset 72 degrees apart from the next adjacent recess (72 degrees multiplied by 5 equals 360 degrees).

Driven member 372, such as a toothed gear, is coupled to dispensing wheels 368 via a common shaft (not shown) such that powering of drive motor 248 operates to drive driven member 372 to rotate dispensing wheels 368 the common number of degrees (i.e. 72 degrees as shown in FIG. 20). In this manner, recess 370 of one dispensing wheel is rotated so as to correlate with the dispensing slot 230' and thereby dispense a single dosage. The recess of three other dispensing wheels may then advance 72 degrees such that the dosage residing within each respective recess is trapped between its respective dispensing wheel 368 and cartridge housing 320 or cover plate 264 (not shown). The remaining dispensing wheel, which was earlier emptied by dispensing its dosage, may advance 72 degrees so as to coincide with its stack of dosages whereby a single dosage 52 is loaded into the empty recess.

To assist loading of dosages 52 into their respective recesses 370, each dispensing channel 366 may include a biasing member 374. One end of biasing member 374 may rest against or be secure to back wall 364 while the opposing end of biasing member 374 engages the stack of dosages within its respective channel 366. Optionally, a biasing plate (not shown) may be placed between biasing member 374 and dosage 52. It is further envisioned that cartridge 360 may be a removable/replaceable cartridge similar to cartridge 270 such that an empty cartridge may be removed from cartridge receiving area 360 while a loaded cartridge may be inserted into the receiving area such that its dispensing channels properly align with dispensing wheels 368.

In accordance with the above, the present invention provides numerous advantages and aspects that are not provided for in the existing art. For example, medication dispensing device 18 operates to dispense controlled substances, such as narcotics, only at the rate designated by the prescribing doctor using, among other components, first and second gates that define a dosage holding area and selectively and controllably dispensing such medication. Further, medication dispensing device 18 is portable so as to provide proper regulation of the patient's drug regimen without requiring the patient to be tied to a non-portable, home-based medication dispenser. Also, medication dispensing device 18 includes security features that operate to record sound data, video data, and/or GPS data, when a breach of device 18 occurs, and transmits such data to a remote monitoring system so that appropriate action may be taken by the owner of device 18 or a third party vendor. Other advantages are also provided.

The foregoing description of the preferred embodiment of the invention has been presented for the purpose of illustration and description. It is not intended to be exhaustive nor is it intended to limit the invention to the precise form disclosed. It will be apparent to those skilled in the art that the disclosed embodiments may be modified in light of the above teachings. The embodiments described are chosen to provide an illustration of principles of the invention and its practical application to enable thereby one of ordinary skill in the art to utilize the invention in various embodiments and with various modifications as are suited to the particular use contemplated. Therefore, the foregoing description is to be considered exemplary, rather than limiting, and the true scope of the invention is that described in the following claims.

The invention claimed is:

1. A medication dispensing device for dispensing a dosage of a medication to a patient, the dosage being dispensed to the patient upon receipt of a valid request, the valid request including an authorized patient identification input and a dosage availability determined in accordance with a medical professional's prescription, the medication dispensing device comprising:
　a) a cartridge unit comprising:
　　i) a cartridge housing having a bottom surface and an upwardly extending sidewall defining a cartridge receiving area, the sidewall further defining a dispensing channel formed therethrough to allow passage of the dosage from the cartridge receiving area to the patient, wherein the dispensing channel is proportioned so that only a single dosage may pass through the dispensing channel at a time, and wherein the dispensing channel is a non-linear channel thereby requiring the dosage to traverse a tortuous path from the cartridge receiving area to the patient;
　　ii) a cartridge configured to reside within the cartridge receiving area and hold one or more dosages;
　　iii) a driven member positioned within the cartridge receiving area and configured to engage the cartridge, the driven member being selectively actuatable to drive the cartridge so as to cause dispensing of a next sequential dosage through the dispensing channel; and
　b) a control unit comprising:
　　i) a main housing configured for removable coupling to the cartridge housing and having a top surface and a downwardly extending sidewall defining a controller receiving area, the downwardly extending side all configured to coincide with the upwardly extending sidewall of the cartridge housing to prevent access to the cartridge receiving area and the controller receiving area;
　　ii) a driver member positioned with the controller receiving area and configured to engage the driven member such that actuation of the driver member upon receipt of the valid request operates to actuate the driven member;
　　iii) a motor driven locking mechanism moveable between locked and unlocked positions, wherein when in the locked position the cartridge unit is secured to the control unit; and wherein when in the unlocked position the cartridge unit is separable from the control unit thereby providing access to the cartridge;
iv) a mobile computing device including a central processing unit (CPU) and a memory, wherein the dosage availability is stored in the memory, the mobile computing device configured to receive the authorized patient identification input; and
v) a battery configured to provide electrical energy to the driver member and the motor driven locking mechanism.

2. The medication dispensing device of claim 1, wherein the cartridge includes a belt having a plurality of outwardly extending fingers defining a plurality of dosage slots therebetween, wherein each slot is configured to contain a respective dosage, and wherein the driven member includes a belt pulley configured to engage the belt, whereby upon receipt of the valid request the driver member is energized to drive rotation of the belt pulley so as to advance the belt until the next sequential dosage becomes aligned with the dispensing channel to dispense the dosage.

3. The medication dispensing device of claim 2, wherein the cartridge is removable and further includes:
a floor integral with and generally perpendicular to the belt and outwardly extending fingers; and
a removable cover having a top panel and a sidewall configured to cover the belt and substantially enclose the dosage slots, wherein the removable cover is removed from the removable cartridge when the removable cartridge resides within the cartridge receiving area.

4. The medication dispensing device of claim 1, further comprising a camera and a microphone, the camera and the microphone configured for recording video data and audio data in the memory upon receipt of an unauthorized patient identification input.

5. The medication dispensing device of claim 1, wherein the driver member is a gear driven by a driver motor, wherein the driver motor is powered by the battery upon receipt of the valid request.

6. The medication dispensing device of claim 1, wherein the upwardly extending sidewall and downwardly extending sidewall include at least one pair of corresponding housing contacts that form a completed circuit when the cartridge unit and control unit are disposed together.

7. The medication dispensing device of claim 6, further comprising a camera and a microphone, wherein the camera and microphone operate to record video data and audio data in the memory upon severing of the completed circuit.

8. The medication dispensing device of claim 7, further comprising a wireless transceiver, and wherein the wireless transceiver operates to transmit the video and audio data to a remote monitoring server.

9. The medication dispensing device of claim 8, further comprising a global positioning system (GPS) node, the GPS node operable to transmit a location of the device to the remote monitoring server upon severing of the competed circuit.

10. The medication dispensing device of claim 1, further comprising a camera, a microphone and a touchscreen display, wherein the mobile computing device is operable to initiate a videoconferencing application program, wherein the patient may remotely engage with a medical professional via a videoconference session.

11. The medication dispensing device of claim 1, wherein the case is about 4 inches wide, about 8 inches long and about 2 inch deep.

12. The medication dispensing device of claim 1, wherein the cartridge includes:
a) a plurality of walls in spaced parallel relation with one another and extending generally perpendicular to the dispensing channel;
b) a back wall extending across a rear edge of the plurality of walls to thereby define a plurality of dosage wells, wherein each of the plurality of dosage wells is configured to contain a stack of dosages;
c) a respective dispensing wheel positioned at a forward edge of the plurality of dosage wells, wherein each dispensing wheel includes a recess configured to receive a single dosage at a time from its respective stack of dosages, and wherein the driven member is coupled to the dispensing wheels, whereupon receipt of the valid request the driver member is energized to drive rotation of the driven member and dispensing wheels so as to advance each respective recess until the next sequential dosage becomes aligned with the dispensing channel thereby dispensing the dosage.

13. The medication dispensing device of claim 12, wherein each recess is rotationally offset a common number of degrees from a next successive recess such that a sum of the common number degrees equals 360 degrees, whereby each valid request causes the driven member to rotate the common number of degrees so as to advance each respective recess until only the next sequential dosage becomes aligned with the dispensing channel, and wherein upon completion of a 360 degree rotation of the driven member and each dispensing wheel, a single dosage is dispensed from each stack.

14. The medication dispensing device of claim 12, wherein each dosage well includes a respective biasing member adjacent the back wall, wherein the biasing member biases its respective stack toward its respective dispensing wheel.

15. A medication dispensing device for dispensing a dosage of a medication to a patient, the dosage being dispensed to the patient upon receipt of a valid request, the valid request including an authorized patient identification input and a dosage availability determined in accordance with a medical professional's prescription, the medication dispensing device comprising:
a) a cartridge unit comprising:
i) a cartridge housing having a bottom surface and an upwardly extending sidewall defining a cartridge receiving area, the sidewall further defining a dispensing channel formed therethrough to allow passage of the dosage from the cartridge receiving area to the patient;
ii) a cartridge configured to reside within the cartridge receiving area and hold one or more dosages;
iii) a driven member positioned within the cartridge receiving area and configured to engage the cartridge, the driven member being selectively actuatable to drive the cartridge so as to cause dispensing of a next sequential dosage through the dispensing channel; and
b) a control unit comprising:
i) a main housing configured for removable coupling to the cartridge housing and having a top surface and a downwardly extending sidewall defining a controller receiving area, the downwardly extending sidewall configured to coincide with the upwardly extending sidewall of the cartridge housing to prevent access to the cartridge receiving area and the controller receiving area;

ii) a driver member positioned with the controller receiving area and configured to engage the driven member such that actuation of the driver member upon receipt of the valid request operates to actuate the driven member;

iii) a motor driven locking mechanism moveable between locked and unlocked positions, wherein when in the locked position the cartridge unit is secured to the control unit, and wherein when in the unlocked position the cartridge unit is separable from the control unit thereby providing access to the cartridge;

iv) a mobile computing device including a central processing unit (CPU) and a memory, wherein the dosage availability is stored in the memory, the mobile computing device configured to receive the authorized patient identification input; and v) a battery configured to provide electrical energy to the driver member and the motor driven locking mechanism, wherein the upwardly extending sidewall and downwardly extending sidewall include at least one pair of corresponding housing contacts that form a completed circuit when the cartridge unit and control unit are disposed together.

16. The medication dispensing device of claim 15, further comprising a camera and a microphone, wherein the camera and microphone operate to record video data and audio data in the memory upon severing of the completed circuit.

17. The medication dispensing device of claim 16, further comprising a wireless transceiver, and wherein the wireless transceiver operates to transmit the video and audio data to a remote monitoring server.

18. The medication dispensing device of claim 17, further comprising a global positioning system (GPS) node, the GPS node operable to transmit a location of the device to the remote monitoring server upon severing of the completed circuit.

19. A medication dispensing device for dispensing a dosage of a medication to a patient, the dosage being dispensed to the patient upon receipt of a valid request, the valid request including an authorized patient identification input and a dosage availability determined in accordance with a medical professional's prescription, the medication dispensing device comprising:

a) a cartridge unit comprising:
i) a cartridge housing having a bottom surface and an upwardly extending sidewall defining a cartridge receiving area, the sidewall further defining a dispensing channel formed therethrough to allow passage of the dosage from the cartridge receiving area to the patient;

ii) a removable cartridge configured to reside within the cartridge receiving area and hold one or more dosages, wherein the cartridge includes a belt having a plurality of outwardly extending fingers defining a plurality of dosage slots therebetween, wherein each dosage slot is configured to contain a respective dosage, wherein the cartridge further includes a floor integral with and generally perpendicular to the belt and outwardly extending fingers, wherein the cartridge further includes a removable cover having a top panel and a sidewall configured to cover the belt and substantially enclose the dosage slots, and wherein the removable cover s removed from the cartridge when the cartridge resides within the cartridge receiving area;

iii) a driven member positioned within the cartridge receiving area and including a belt pulley configured to engage the belt; the driven member being selectively actuatable to drive the cartridge so as to cause dispensing of a next sequential dosage through the dispensing channel; and b) a control unit comprising:
i) a main housing configured for removable coupling to the cartridge housing and having a top surface and a downwardly extending sidewall defining a controller receiving area, the downwardly extending sidewall configured to coincide with the upwardly extending sidewall of the cartridge housing to prevent access to the cartridge receiving area and the controller receiving area;

ii) a driver member positioned with the controller receiving area and configured to engage the driven member such that actuation of the driver member upon receipt of the valid request operates to actuate the driven member to drive rotation of the belt pulley so as to advance the belt until the next sequential dosage becomes aligned with the dispensing channel to dispense the dosage;

iii) a motor driven locking mechanism moveable between locked and unlocked positions, wherein when in the locked position the cartridge unit is secured to the control unit, and wherein when in the unlocked position the cartridge unit is separable from the control unit thereby providing access to the cartridge;

iv) a mobile computing device including a central processing unit (CPU) and a memory, wherein the dosage availability is stored in the memory, the mobile computing device configured to receive the authorized patient identification input; and v) a battery configured to provide electrical energy to the driver member and the motor driven locking mechanism.

* * * * *